US008097260B2

(12) United States Patent
Apicella et al.

(10) Patent No.: US 8,097,260 B2
(45) Date of Patent: Jan. 17, 2012

(54) **LIPID A DEFICIENT MUTANTS OF *NEISSERIA MENINGITIDIS***

(76) Inventors: Michael A. Apicella, Solon, IA (US); Deborah Post, Fairfax, CA (US)

(*) Notice: Subject to any disclaimer, the term of this patent is extended or adjusted under 35 U.S.C. 154(b) by 357 days.

(21) Appl. No.: 12/254,681

(22) Filed: Oct. 20, 2008

(65) Prior Publication Data

US 2010/0003283 A1 Jan. 7, 2010

Related U.S. Application Data

(63) Continuation of application No. 10/652,857, filed on Aug. 29, 2003, now Pat. No. 7,438,918.

(60) Provisional application No. 60/407,499, filed on Aug. 30, 2002.

(51) Int. Cl.
*A61K 39/095* (2006.01)
*A61K 39/02* (2006.01)
*A61K 39/00* (2006.01)
*A01N 63/00* (2006.01)

(52) U.S. Cl. ............... 424/250.1; 424/200.1; 424/234.1; 424/184.1; 424/93.2; 424/94.4

(58) Field of Classification Search ........................ None
See application file for complete search history.

(56) References Cited

U.S. PATENT DOCUMENTS

| | | | |
|---|---|---|---|
| 4,533,630 | A | 8/1985 | Wilkins et al. |
| 4,559,157 | A | 12/1985 | Smith et al. |
| 4,608,392 | A | 8/1986 | Jacquet et al. |
| 4,820,508 | A | 4/1989 | Wortzman |
| 4,992,478 | A | 2/1991 | Geria |
| 5,976,536 | A | 11/1999 | Stephens et al. |

FOREIGN PATENT DOCUMENTS

| | | |
|---|---|---|
| EP | 184187 | 6/1986 |
| WO | WO 01/09350 A2 * | 2/2001 |
| WO | WO 01/09350 A2 | 8/2001 |

OTHER PUBLICATIONS

Illustrated Stedman's Medical Dictionary, 24th Edition, p. 707, 1982.*

Webster's II New Riverside University Dictionary, p. 993, 1984.*

"AF428103—Neisseria meningitidis acyl-transferase MsbB (msbB) gene, complete", Genbank Accession Number, Entrez Nucleotide—NCBI, (Feb. 2002), 2 pages.

Altshul et al., "Basic Local Alignment Search Tool," *J.Mol. Biol.*, 1990, 215:403-410.

Altshul et al., "Gapped BLAST and PSI-BLAST: a new generation of protein database search programs," *Nucl. Acids Res.*, 1997, 25(17):3389-3402.

Apicella, Michael A., "Gram-Negative Cocci", Mandell, Douglas, and Bennett's Principles and Practice of Infectious Diseases, Gerald L. Mandell; R. Gordon Douglas; John E. Bennett; Raphael Dolin, 5th ed. Philadelphia : *Churchill Livingstone, ISBN*: 044307593X 0443079838 (v. 1) 0443075247 (v. 2), (2000), 2228-2241.

Apicella, Michael A., et al., "Modification by sialic acid of *Neisseria gonorrhoeae* lipooligosaccharide epitope expression in human urethral exudates: an immunoelectron microscopic analysis", *Journal of Infectious Diseases*, 162(2), (Aug. 1990), 506-512.

Batzer, et al., "Enhanced evolutionary PCR using oligonucleotides with inosine at the 3'-terminus," *Nucl. Acids Res.*, 1991, 19(18):5081.

Brozek, Kathryn A., et al., "Biosynthesis of Lipid A in *Escherichia coli", J. Biol.Chem.*, 265, (1990), 15410-15417.

Clementz, Tony, et al., "Function of the *Escherichia coli* msbB Gene, a Multicopy Suppressor of htrB Knockouts, in the Acylation of Lipid A", *The Journal of Biological Chemistry*, 272, (1997), 10353-10360.

Corpet, et al., "Multiple sequence alignment with hierarchical clustering," *Nucl. Acids Res.*, 1988, 16(22):10881-10890.

Granoff, et al., "Effect of immunity to the carrier protein on antibody responses to *Haemophilus influenzae* type b conjugate vaccines." *Vaccine* 11: S46-S51, 1993.

Hanahan, "Studies on Transformation of *Escherichia coli* with Plasmids," *J. Mol. Biol.*, 1983, 166:557-580.

Harvey, H. A., et al., "Receptor-mediated endocytosis of *Neisseria gonorrhoeae* into primary human urethral epithelial cells: the role of the asialoglycoprotein receptor", *Molecular Microbiology.* 42(3) (Nov. 2001), 659-672.

Harvey, et al., "Immortalization of Human Urethral Epithelial Cells: a Model for the Study of the Pathogenesis of and the Inflammatory Cytokine Response to *Neisseria gonorrhoeae* Infection," *Infect. Immun.*, 2002, 70(10):5808-5815.

Higgins and Sharp, "Fast and sensitive multiple sequence alignments on a microcomputer," *CABIOS*, 1989, 5(2):151-153.

Higgins and Sharp, "CLUSTAL: a package for performing multiple sequence alignment on a microcomputer," *Gene*, 1988, 73:237-244.

Huang, et al., "Parallelization of a local similarity algorithm," *CABIOS*, 1992, 8(2):155-165.

Jones, Bradley D., et al., "Study of the Role of the htrB Gene in *Salmonella typhimurium* Virulence", *Infection and Immunity*, 65 (11), (1997), 4778-4783.

Karlin and Altschul, "Methods for assessing the statistical significance of molecular sequence features by using general scoring schemes," *Proc. Natl. Acad. Sci. USA*, 1990, 87:2264-2268.

Karlin and Altschul, "Applications and statistics for multiple high-scoring segments in molecular sequences," *Proc. Natl. Acad. Sci. USA*, 1993, 90:5873-5877.

Karow, Margaret L., et al., "Isolation and Characterization of the *Escherichia coli* htrB Gene, Whose Product is Essential for Bacterial Viability Above 33 degrees C in Rich Media", *Journal of Bacteriology*, 173, (1991), 741-750.

Kulshin, Vladimir A., et al., "Structural characterization of the lipid A component of pathogenic *Neisseria meningitidis*", *Journal of Bacteriology*, 174(6), (Mar. 1992), 1793-1800.

Lee, Na-Gyong, et al., "Mutation of the htrB Locus of *Haemophilus influenzae* Nontypable Strain 2019 is Associated with Modifications of Lipid A and Phosphorylation of the Lipo-oligosaccharide", *J. Biol. Chem.*, 270, (1995), 27151-27159.

Lesse et al., "Increased resolution of lipopolysaccharides and lipooligosaccharides utilizing tricine-sodium dodecyl sulfate-polyacrylamide gel electrophoresis," *J. Immunol. Meth.*, 1990, 126:109-117.

Mandrell et al., "Lipooligosaccharides (LOS) of *Neisseria gonorrhoeae* and *Neisseria meningitides* Have Components That are Immunochemically Similar to Precursors of Human Blood Group Antigens," *J. Exp. Med.*, 1988, 168:107-126.

(Continued)

*Primary Examiner* — S. Devi

(74) *Attorney, Agent, or Firm* — Viksnins Harris & Padys PLLP

(57) ABSTRACT

The invention provides lipid A deficient mutant *Neisseria meningitidis* cells, pharmaceutical compositions incorporating such cells, and methods of using such cells.

8 Claims, 8 Drawing Sheets

OTHER PUBLICATIONS

McGhee et al., "New Perspectives in Mucosal Immunity With Emphasis on Vaccine Develoment," *Sem. Hematol.*, 1993, 30(4):3-15.

Meinkoth and Wahl, "Hybridization of Nucleic Acids Immobilized on Solid Supports," *Anal. Biochem.* 1984, 138:267-284.

Melaugh et al., "Partial Characterization of the Major Lipooligosaccharide from a Strain of *Haemophilus ducreyi*, the Causative Agent of Chancroid, a Genital Ulcer Disease," *J. Biol. Chem.*, 1992, 267(19):13434-13439.

Menard et al., "Nonpolar Mutagenesis of the ipa Genes Defines IpaB, IpaC, and IpaD as Effectors of Shigella flexneri Entry into Epithelial Cells," *J. Bacteriol.*, 1993, 175(18):5899-5906.

Munkley et al., "Blocking of bactericidal killing of *Neisseria meningitidis* by antibodies directed against class 4 outer membrane protein," *Microb. Pathog.*, 1991, 11:447-452.

Myers and Miller, "Optimal alignments in linear space," *CABIOS*, 1988, 4(1):11-17.

Needleman and Wunsch, "A General Method Applicable to the Search for Similarities in the Amino Acid Sequence of Two Proteins," *J. Mol. Biol.*, 1970, 443-453.

Nichols, W. A., et al., "htrB of *Haemophilus influenzae*: Determination of Biochemical Activity and Effects on Virulence and Lipooligosaccharide Toxicity", *Journal of Endotoxin Research*, 4., (1997), 163-172.

Ohtsuka et al., "An Alternative Approach to Deoxyoligonucleotides as Hybridization Probes by Insertion of Deoxyinosine at Ambiguous Codon Positions," *JBC*, 1985, 260(5):2605-2608.

Pearson and Lipman, "Improved tools for biological sequence comparision," *Proc. Natl. Acad. Sci.* USA, 1988, 85:2444-2448.

Pearson, "Using the FASTA Program to Search Protein and DNA Sequence Databases," *Meth. Mol. Biol.*, 1994, 24:307-331.

Pederson and Reeh, "Analysis of the Proteins Synthesized in Ultraviolet Light-Irradiated *Escherichia coli* Following Infection with the Bacteriophages .lamda.drif.sup.d 18 and .lamda.dfus-3," *Mol. Gen. Genet.*, 1976, 144:339-343.

Post, Deborah M., et al., "Intracellular survival of *Neisseria gonorrhoeae* in male urethral epithelial cells: importance of a hexaacyl lipid A", *Infection & Immunity.* 70(2), (Feb. 2002), 909-920.

Post, Deborah M., et al., "The msbB mutant of *Neisseria menigitidis* strain NMB has a defect in lipooligosaccharide assembly and transport to the outer membrane", *Infection and Immunity*, 71(2), (Feb. 2003), 647-655.

Preston, Andrew, et al., "The Lipooligosaccharides of Pathogenic Gram-Negative Bacteria", *Critical Review in Microbiology*, 22., (1996), 139-180.

Pridemore et al., "A Lipopolysaccharide-Deficient Mutant of *Neisseria meningitidis* Elicits Attenuated Cytokine Release by Human Macrophages and Signals via Toll-like Receptor (TLR) 2 but Not via TLR4/MD2," *J. Inf. Dis* 2001, 183:89-96.

Raetz, Christian R., et al., "Bacterial endotoxins: extraordinary lipids that activate eucaryotic signal transduction", *Journal of Bacteriology.* 175(18) (Sep. 1993), 5745-5753.

Raetz, Christian R., et al., "Gram-negative endotoxin: an extraordinary lipid with profound effects on eukaryotic signal transduction", *FASEB Journal.* 5(12)., (Sep. 1991), 2652-2660.

Richmond, Peter, et al., "Evaluation of De-O-Acetylated Meningococcal C Polysachharide-Tetanus Toxoid Conjugate Vaccine in Infancy: Reactogenicity, Immunogenicity, Immunologic Priming, and Bactericidal Activity against O-Acetylated and De-O-Acetylated Serogroup C Strains", *Infection and Immunity*, 69 (4), (Apr. 2001), 2378-2382.

Rosenqvist et al., "Functional Activities and Epitope Specificity of Human and Murine Antibodies against the Class 4 Outer Membrane Protein (Rmp) of *Neisseria meningitidis*," *Infect. Immun.*, 1999, 67(3):1267-1276.

Rossolini et al., "Use of deoxyinosine-containing primers vs degenerate primers for polymerase chain reaction based on ambiguous sequence information," *Mol. Cell. Probes*, 1994, 8:91-98.

Schnaitman, Carl A., et al., "Genetics of lipopolysaccharide biosynthesis in enteric bacteria", *Microbiological Reviews.* 57( (Sep. 1993), 655-682.

Smith and Waterman, "Comparision of Biosequences," *Adv. Appl. Math.* 1981, 2:482-489.

Somerville, Jr., John E., et al., "A Novel *Escherichia coli* Lipid A Mutant That Produces an Antiinflammatory Lipopolysaccharide", *J. Clin. Invest.*, 97, (1996), 359-365.

Steeghs et al., "Immunity of Outer Membrane Proteins in a Lipopolysaccharide-Deficient Mutant of *Neisseria meningitidis*: Influence of Adjuvants on the Immune Response," *Infect. Immun.*, 1999, 67(10):4988-4993.

Steeghs, Liana, et al., "*Meningitis bacterium* is viable without endotoxin", *Nature.* 392(6675), (Apr. 1998), 449-50.

Steeghs, Liana, et al.,"Outer membrane composition of a lipopolysaccharide- deficient *Neisseria meningitidis* mutant", *EMBO Journal.* 20(24)., (Dec. 2001), 6937-6945.

Stephens et al., "Insertion of Tn916 in *Neisseria meningitidis* Resulting in Loss of Group B Capsular Polysaccharide," *Infect. Immun.*, 1991, 59(11):4097-4102.

Stephens et al., "Tn916-Generated Lipooligosaccharide Mutants of *Neisseria meningitidis* and *Neisseria gonorrhoeae*," *Infect. Immun.*, 1994, 62(7):2947-2952.

Sunshine, Melvin G., et al., "Mutation of the htrB Gene in a Virulent *Salmonella typhimurium* Strain by Intergeneric Transduction: Strain Construction and Phenotypic Characterization", *Journal of Bacteriology*, 179, (1997), 5521-5533.

Towbin et al., "Electrophoretic transfer of proteins from polyacrylamide gels to nitrocellulose sheets: Procedure and some applications," *Proc. Natl. Acad. Sci, USA*, 1979, 76(9):4350-4354.

Tsai and Frasch, "A Sensitive Silver Stain for Detecting Lipopolysaccharides in Polyacrylamide Gels," *Anal. Biochem.*, 1982, 119:115-119.

Tzeng et al., "Endotoxin of *Neisseria meningitidis* Composed Only of Intact Lipid A: Inactivation of the Meningococcal 3-Deoxy-D-Manno-Octulosonic Acid Transferase," *J. Bacteriol.*, 2002, 184(9):2379-2388.

Tzeng et al., "KpsF is the Arabinose-5-phosphate Isomerase Required for 3-Deoxy-D-manno-octulosonic Acid Biosynthesis and for Both Lipooligosaccharide Assembly and Capsular Polysaccharide Expression in *Neisseria meningitidis*," *J. Biol. Chem.*, 2002, 277(27):24103-24113.

Uronen et al., "Gram-negative bacterial induce proinflammatory cytokine production by monocytes in the absence of lipopolysaccharide (LPS)," *Clin. Exp. Immunol.*, 2000, 122:312-315.

Van Der Ley, Peter, et al., "Modification of lipid A biosynthesis in *Neisseria meningitidis* IpxL mutants: influence on lipopolysaccharide structure, toxicity, and adjuvant activity", *Infection & Immunity.* 69(10), (Oct. 2001), 5981-5990.

Vogel, Ulrich, "Mechanisms of Neisserial Serum Resistance", *Molecular Microbiology*, 32 (1999), 1133-1139.

West, David, et al., "Recombinant *Neisseria meningitidis* transferrin binding protein A protects against experimental meningococcal infection", *Infection & Immunity* 69(3)., (Mar. 2001), 1561-1567.

Whitfield, "Biosynthesis of lipopolysaccharide O antigens," *Trends Microbiol.*, 1995, 3(5):178-185.

Zhang, Q., et al., "Primary and booster mucosal immune responses to meningococcal group A and C conjugate and polysaccharide vaccines administered to university students in the United Kingdom", *Infection & Immunity.* 69(7)., (Jul. 2001), 4337-4341.

* cited by examiner

A 1          2          3

B 1    2    3

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: A primer

<400> SEQUENCE: 1
caacaggcgg cggtggaaca g                                              21

<210> SEQ ID NO 2
<211> LENGTH: 21
<212> TYPE: DNA
<213> ORGANISM: Artificial Sequence
<220> FEATURE:
<223> OTHER INFORMATION: A primer

<400> SEQUENCE: 2
ttcggcatcc actcccsttt g                                              21

<210> SEQ ID NO 3
<211> LENGTH: 882
<212> TYPE: DNA
<213> ORGANISM: Neisseria meningitidis

<400> SEQUENCE: 3
atgtgtatcg agatgaaatt tatatttttt gtactgtatg ttttgcagtt tctgccgttt      60
gcgctgctgc acaaacttgc cgacctgacg ggtttgctcg cctacctttt ggtcaaaccc     120
cgccgccgta tcggcgaaat caatttggca aaatgctttc ccgagtggga cggaaaaaag     180
cgcgaaaccg tattgaagca gcatttcaaa catatggcga aactgatgct tgaatacggc     240
ttatattggt acgcgcctgc cgggcgtttg aaatcgctgg tgcgttaccg caataagcat     300
tatttggacg acgcgctggc ggcggggggaa aaagtcatca ttctgtaccc gcacttcacc     360
gcgttcgaga tggcggtgta cgcgcttaat caggatgtac cgctgatcag tatgtattcc     420
```

-continued

```
caccaaaaaa acaagatatt ggacgcacag attttgaaag gccgcaaccg ctacgacaat    480
gtcttcctta tcgggcgcac cgaagggctg cgcgccctcg tcaaacagtt ccgcaaaagc    540
agcgcgccgt ttctgtatct gcccgatcag gatttcggac gcaacgattc ggttttgtg    600 gattttttcg gtattcagac ggcaacgatt accggcttga gccgcattgc cgcgcttgca    660
aatgcaaaag tgatacccgc catccccgtc cgcgaggcgg acaataccgt tacattgcat    720
ttctacccgg cttgggaatc ctttccgagt gaagatgcgc aggccgacgc gcagcgcatg    780
aaccgtttta tcgaggaacg cgtgcgcgaa catcccgagc agtattttg gctgcacaag    840 cgtttcaaaa cccgtccgga aggcagcccc gattttact ga                       882
```

<210> SEQ ID NO 4
<211> LENGTH: 293
<212> TYPE: PRT
<213> ORGANISM: Neisseria meningitidis

<400> SEQUENCE: 4

```
Met Cys Ile Glu Met Lys Phe Ile Phe Phe Val Leu Tyr Val Leu Gln
  1               5                  10                  15

Phe Leu Pro Phe Ala Leu Leu His Lys Leu Ala Asp Leu Thr Gly Leu
             20                  25                  30

Leu Ala Tyr Leu Leu Val Lys Pro Arg Arg Arg Ile Gly Glu Ile Asn
         35                  40                  45

Leu Ala Lys Cys Phe Pro Glu Trp Asp Gly Lys Lys Arg Glu Thr Val
     50                  55                  60

Leu Lys Gln His Phe Lys His Met Ala Lys Leu Met Leu Glu Tyr Gly
 65                  70                  75                  80

Leu Tyr Trp Tyr Ala Pro Ala Gly Arg Leu Lys Ser Leu Val Arg Tyr
                 85                  90                  95

Arg Asn Lys His Tyr Leu Asp Asp Ala Leu Ala Ala Gly Glu Lys Val
            100                 105                 110

Ile Ile Leu Tyr Pro His Phe Thr Ala Phe Glu Met Ala Val Tyr Ala
        115                 120                 125

Leu Asn Gln Asp Val Pro Leu Ile Ser Met Tyr Ser His Gln Lys Asn
    130                 135                 140

Lys Ile Leu Asp Ala Gln Ile Leu Lys Gly Arg Asn Arg Tyr Asp Asn
145                 150                 155                 160

Val Phe Leu Ile Gly Arg Thr Glu Gly Leu Arg Ala Leu Val Lys Gln
                165                 170                 175

Phe Arg Lys Ser Ser Ala Pro Phe Leu Tyr Leu Pro Asp Gln Asp Phe
            180                 185                 190

Gly Arg Asn Asp Ser Val Phe Val Asp Phe Phe Gly Ile Gln Thr Ala
        195                 200                 205

Thr Ile Thr Gly Leu Ser Arg Ile Ala Ala Leu Ala Asn Ala Lys Val
    210                 215                 220

Ile Pro Ala Ile Pro Val Arg Glu Ala Asp Asn Thr Val Thr Leu His
225                 230                 235                 240

Phe Tyr Pro Ala Trp Glu Ser Phe Pro Ser Glu Asp Ala Gln Ala Asp
                245                 250                 255

Ala Gln Arg Met Asn Arg Phe Ile Glu Glu Arg Val Arg Glu His Pro
            260                 265                 270
```

```
-continued

Glu Gln Tyr Phe Trp Leu His Lys Arg Phe Lys Thr Arg Pro Glu Gly
        275                 280                 285

Ser Pro Asp Phe Tyr
    290
```

LIPID A DEFICIENT MUTANTS OF NEISSERIA MENINGITIDIS

CROSS-REFERENCE TO RELATED APPLICATION

This application is a continuing application of U.S. application Ser. No. 10/652,857, which was filed on Aug. 29, 2003 and issued as U.S. Pat. No. 7,438,918 on Oct. 21, 2008, which application claims priority of invention under 35 U.S.0 §119 (e) from U.S. application Ser. No. 60/407,499 filed Aug. 30, 2002, the disclosure of which is incorporated by reference herein.

STATEMENT OF GOVERNMENT RIGHTS

The invention was made with the support of NIH Grant Numbers AI45728, AI44642, and T32AI07511. The U.S. Government has certain rights in the invention.

BACKGROUND OF THE INVENTION

*Neisseria meningitidis* is one of the leading causes of bacterial meningitis worldwide, affecting mainly children and young adults (Apicella, 2000). The rapid progression of meningococcal disease makes proper diagnosis and subsequent treatment often vital to the survival of infected individuals. If not properly diagnosed and treated, meningococcal infections can lead to shock and death within a matter of hours (West et al., 2001). Thus, better prevention, diagnosis and treatment of meningococcal infections would be invaluable.

*N. meningitidis* virulence factors include the bacteria's capsular polysaccharide, which protects the bacteria from host immune defenses; lipooligosaccharide (LOS), which is the principle glycolipid present in the bacteria's outer membrane and is composed of the oligosaccharide chain extensions, the core, and the lipid A; and class 4 outer membrane protein (OMP), also called reduction modifiable protein (Rmp). Vaccines that contain LOS may have both positive and negative side effects. For example, the LOS may function as a natural adjuvant. However, because of toxicity from the LOS, the use of the vaccine may be limited.

*N. meningitidis* that do not express one or more virulence factors, e.g., lipid A, which are readily grown in culture and are immunogenic, would be useful to prepare vaccines and as tools for the generation of immunological reagents.

SUMMARY OF THE INVENTION

The present invention provides a transgenic *Neisseria meningitidis* cell including a disrupted msbB gene, wherein the cell has reduced lipooligosaccharide (LOS) as compared to a corresponding wild-type *Neisseria meningitidis* cell. The msbB gene may be disrupted by mutagenesis, and the mutagenesis may be a deletion, insertion or substitution mutagenesis, or a combination thereof. The cell may have reduced LOS in its outer membrane as compared to a corresponding wild-type *Neisseria meningitidis* cell, and the cell may have reduced lipid A components present in the cell's outer membrane as compared to a corresponding wild-type *Neisseria meningitidis* cell. Furthermore, the cell may have reduced toxicity as compared to a corresponding wild-type *Neisseria meningitidis* cell. In one embodiment, the cell is a *Neisseria meningitidis* NMBA11K3 cell. *Neisseria meningitidis* strain NMBA11K3 was deposited on Dec. 1, 2005 with the American Type Culture Collection, 10801 University Blvd., Manassas, Va. 20110-2209 under the provisions of the Budapest Treaty, and all restrictions will be irrevocably removed upon the granting of a patent on this application. NMBA11K3 has been accorded accession number PTA-7257. The present invention also provides an antibody specific for the transgenic *Neisseria meningitidis* cells. In some embodiments, the antibody is a monoclonal or polyclonal antibody.

The present invention also provides an isolated and purified polynucleotide including a nucleic acid sequence encoding an msbB gene from *Neisseria meningitidis*. In one embodiment, the polynucleotide includes SEQ ID NO:3.

The present invention also provides an isolated and purified polypeptide including a MsbB polypeptide from *Neisseria meningitidis*. In one embodiment, the polypeptide includes SEQ ID NO:4.

The present invention further provides a pharmaceutical composition including a transgenic *Neisseria meningitidis* cell including a disrupted msbB gene, wherein the cell has reduced lipooligosaccharide (LOS) as compared to a corresponding wild-type *Neisseria meningitidis* cell, and a pharmaceutically acceptable carrier, wherein the composition is capable of eliciting an immune response against *Neisseria meningitidis*. The composition may further include an effective amount of an immunological adjuvant. The transgenic cell may have reduced LOS in its outer membrane as compared to a corresponding wild-type *Neisseria meningitidis* cell, and the cell may have reduced lipid A components present in the cell's outer membrane as compared to a corresponding wild-type *Neisseria meningitidis* cell. Furthermore, the cell may have reduced toxicity as compared to a corresponding wild-type *Neisseria meningitidis* cell.

The present invention also provides a method of eliciting an immune response in a subject against *Neisseria meningitidis* including administering to a subject the pharmaceutical composition as described hereinabove and also provides a method of preventing *Neisseria meningitidis* infection including administering to a subject the pharmaceutical as described hereinabove. In some embodiments of the invention, the pharmaceutical composition is administered orally, mucosally or by subcutaneous or intramuscular injection. In some embodiments, the pharmaceutical composition is administered mucosally via a nasal, gastrointestinal or genital site.

BRIEF DESCRIPTION OF THE FIGURES

(FIG. 2A) Silver staining analysis of an SDS-PAGE gel. Lane 1: NMB LOS; Lane 2: NMBcap- LOS; Lane 3: NMBA11K3cap-LOS. The sialylated LOS (top band) is absent from the NMB-cap-LOS because the sialylation genes were deleted in this strain. A different glycoform of LOS is visible in the NMB-cap- LOS sample where the sialylated LOS band would normally migrate. (FIG. 2B) Western blot analysis with mAb 6B4. Lane 1: NMB LOS; Lane 2: NMBcap- LOS; Lane 3: NMBA11K3cap- LOS.

(FIG. 3A) NMB, (FIG. 3B) NMBA11K3, (FIG. 3C) NMBcap-, and (FIG. 3D) NMBA11K3cap- (Scale bars indicate 1 micron); (FIG. 3E)

Figure 1:
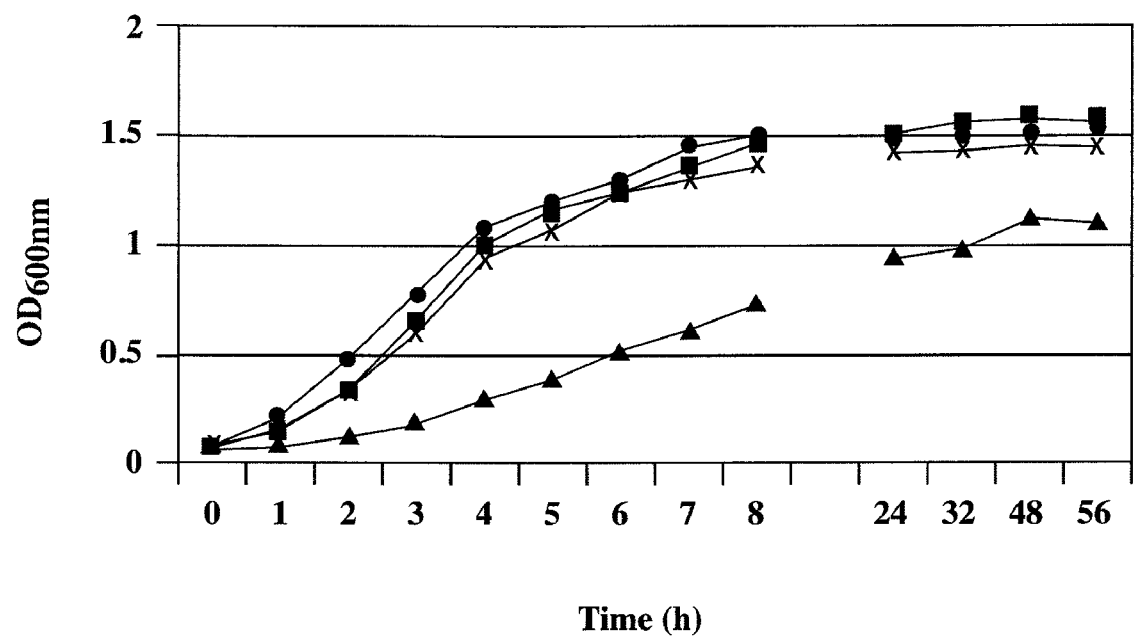
FIG. 1. Growth curves from strains NMB (diamond), NMBcap- (square), NMBA11K3 (triangle), and NMBA11K3cap- (asterisk). Data shown is representative of three separate experiments.
Figure 2:
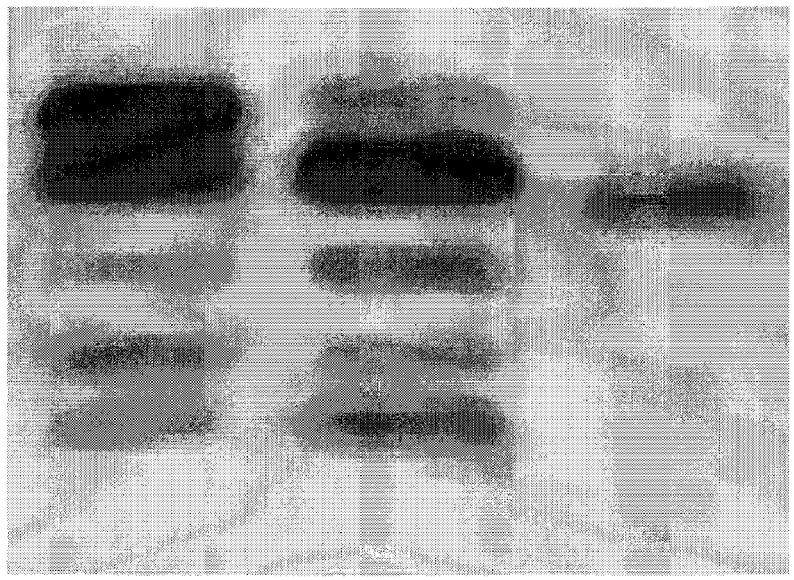
FIGS. 2A and 2B. Characterization of NMBA11K3cap-LOS by SDS-PAGE and Western blot analyses.
Figure 2:
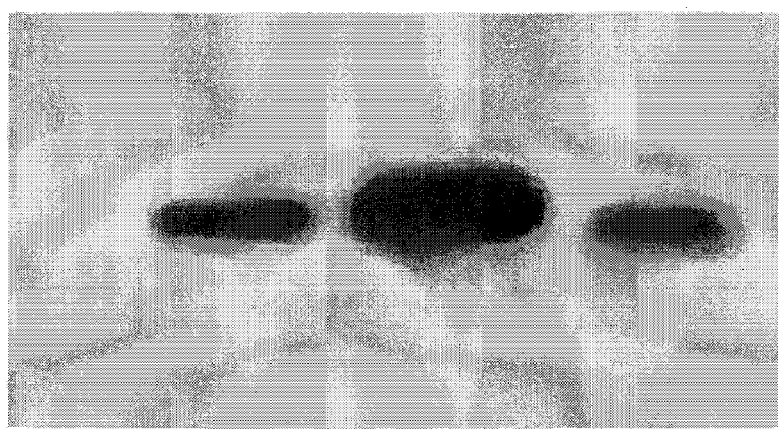
Figure 3:
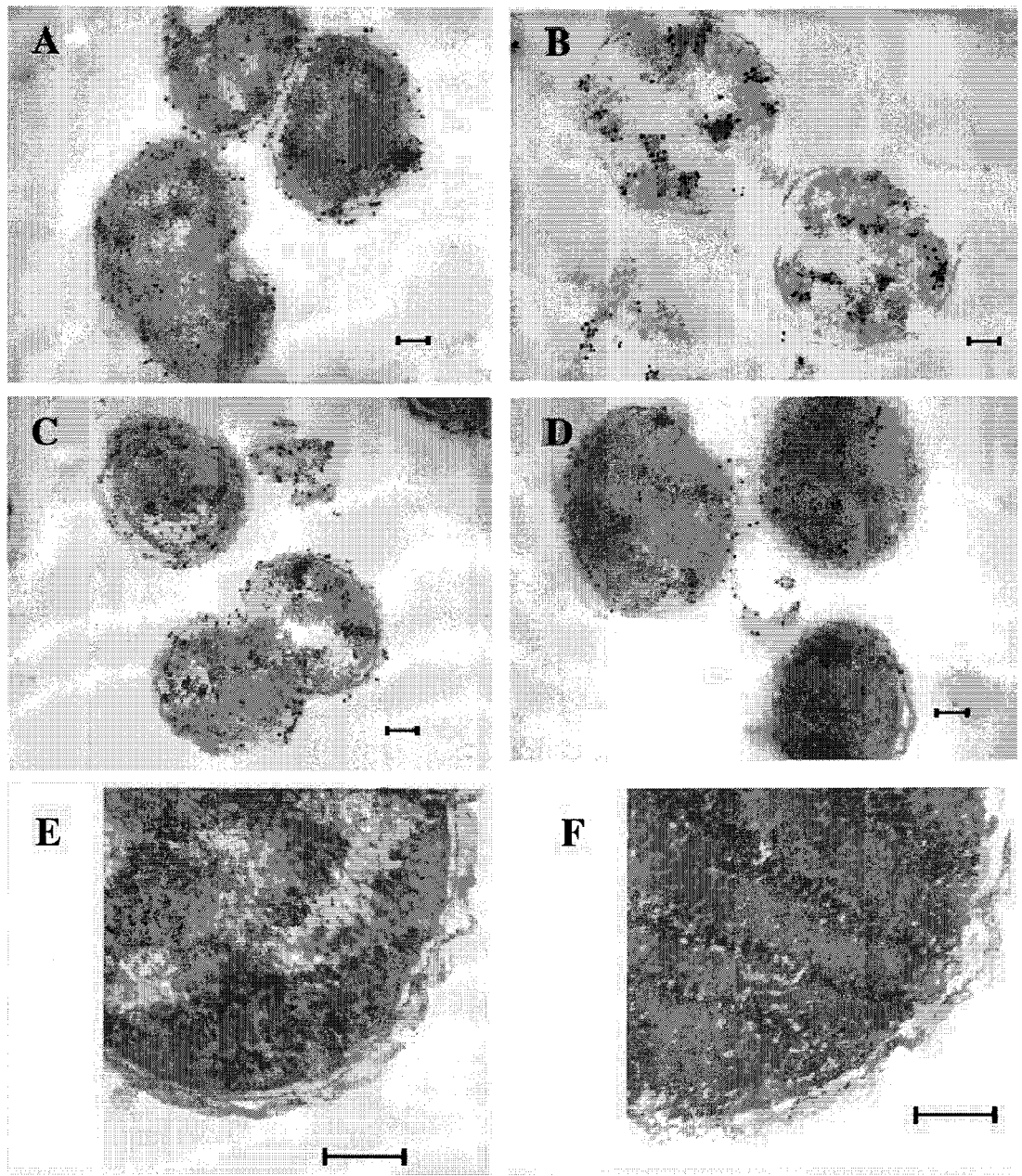
FIGS. 3A-3F. Examination of mAb 6B4 immunolabeled *N. meningitidis* bacteria using TEM analyses.
Figure 4:
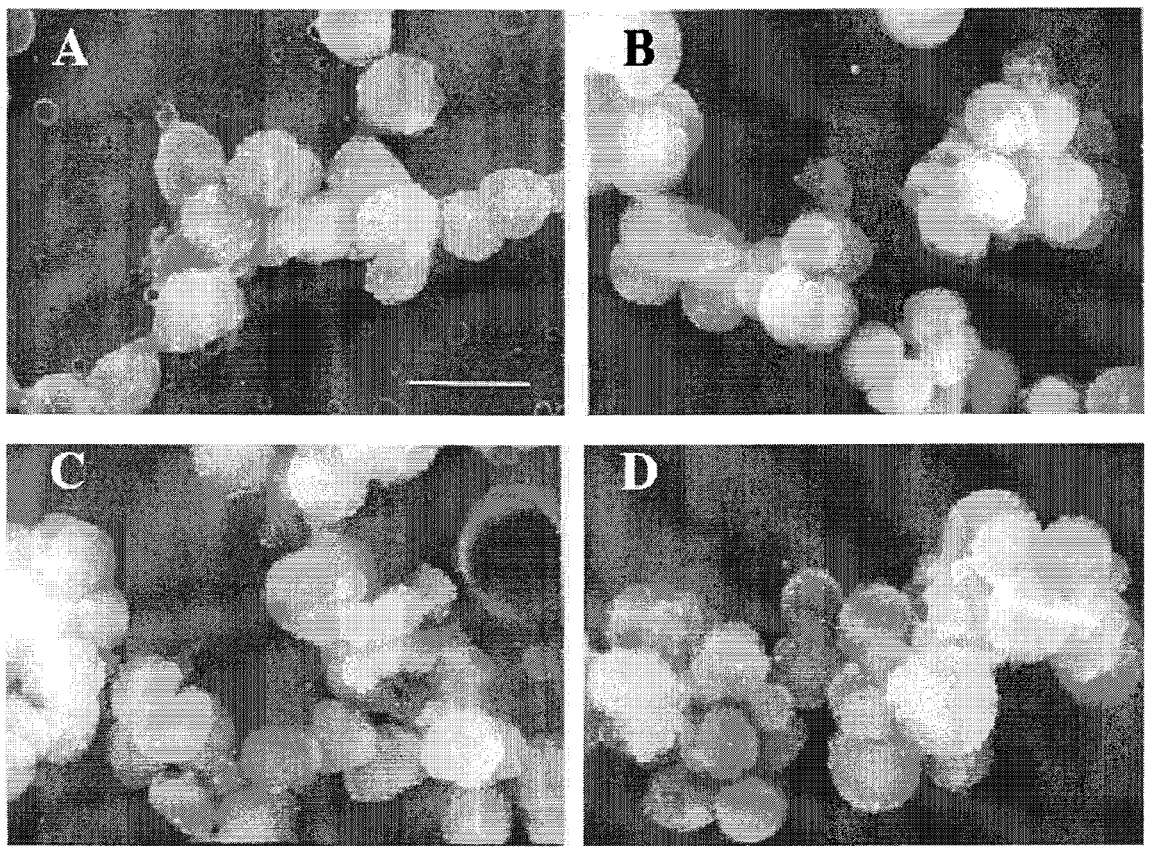

NMB and (FIG. 3F) NMBA11K3 are Epon-embedded sections showing the structure of the bacterial cell membranes (Scale bars indicate 100 nm).

FIGS. 4A-4D. SEM analyses of mAb 6B4 immunolabeled *N. meningitidis* bacteria. (FIG. 4A) NMB, (FIG. 4B) NMBA11K3, (FIG. 4C) NMBcap-, and (FIG. 4D) NMBA11K3cap- (Scale bar indicates 100 nm).

Figure 5:
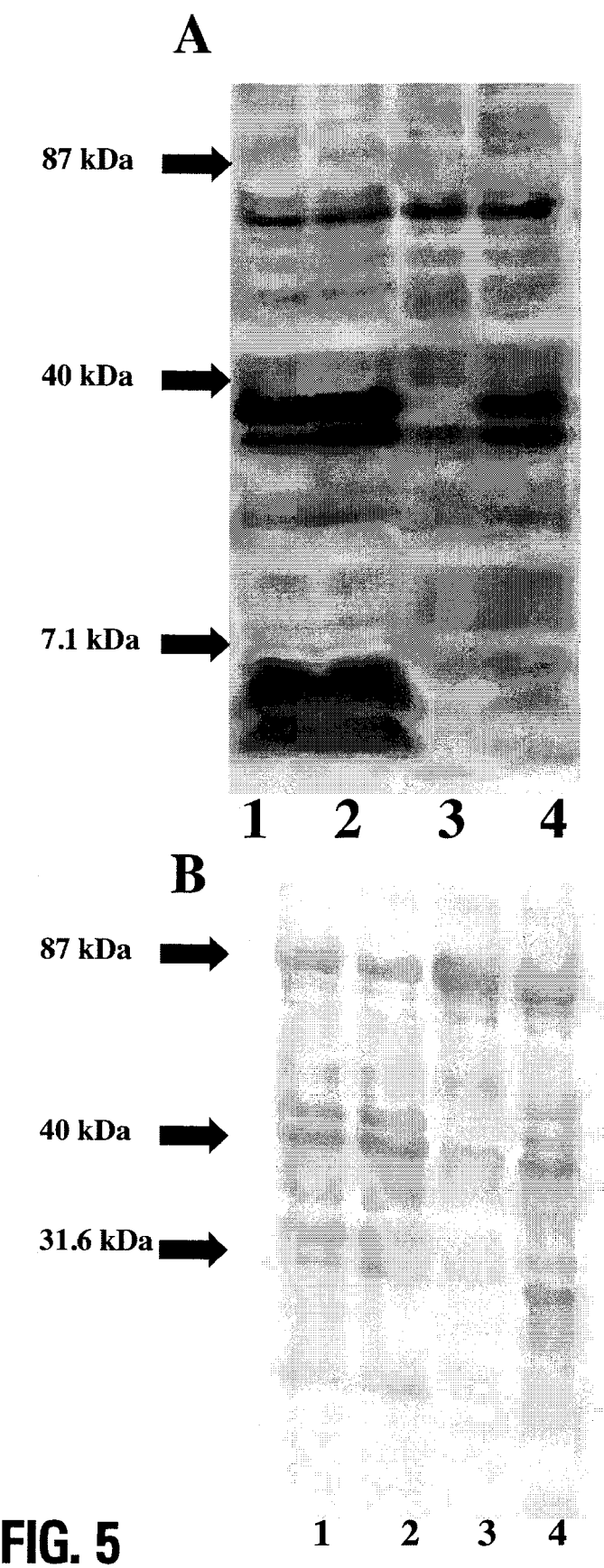

FIGS. 5A and 5B. (FIG. 5A) Silver staining and (FIG. 5B) Coomassie blue staining analyses of MPs from *N. meningitidis* strains: (1) NMB, (2) NMBcap-, (3) NMBA11K3, and (4) NMBA11K3cap-.

Figure 6:
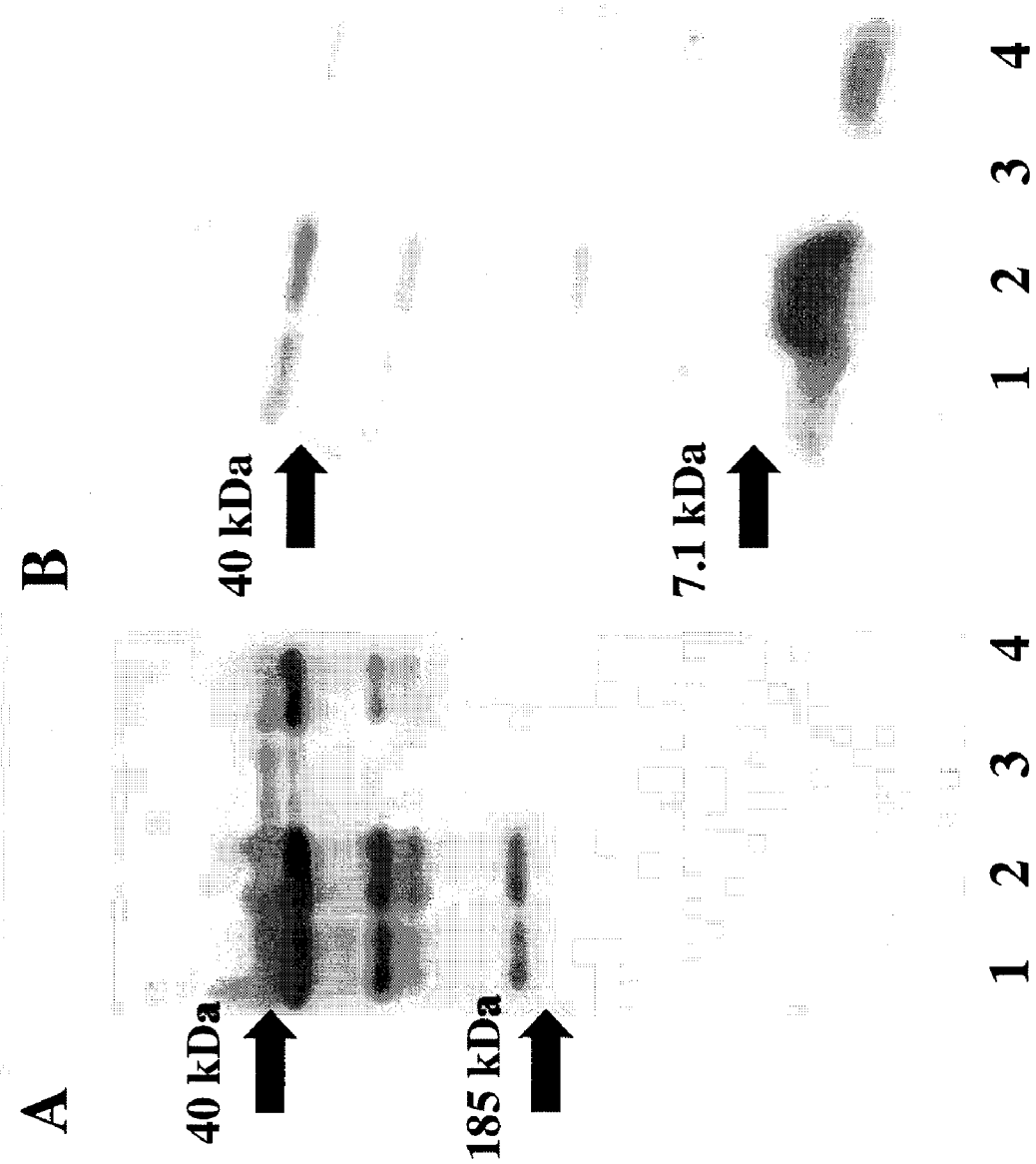

FIGS. 6A and 6B. Western blot analyses of MPs from *N. meningitidis* strains: (1) NMB, (2) NMBcap-, (3) NMBA11K3, (4) NMBA11K3cap-. (FIG. 6A) mAb 3H1 for porin, and (FIG. 6B) mAb 6B4 for LOS.

FIGS. 7A-7D. GC/MS chromatograms of fatty acid methyl esters derived from the membrane preparations of the designated *N. meningitidis* strains: (FIG. 7A) NMB, (FIG. 7B) NMBcap-, (FIG. 7C) NMBA11K3, (FIG. 7D) NMBA11K3 cap-. Relevant peaks are labeled in each chromatogram. Y-axes show the relative peak intensities of the summed ion abundancies.

DETAILED DESCRIPTION OF THE INVENTION

I. Definitions

The term "chimeric" refers to any gene or DNA that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may include regulatory sequences and coding sequences that are derived from different sources, or include regulatory sequences and coding sequences derived from the same source, but arranged in a manner different from that found in nature.

As used herein, "disrupted gene" refers to an insertion, substitution, or deletion either in a gene of interest or in the vicinity of the gene, i.e., upstream (5') or downstream (3') of the gene, which results in the reduction of the biological activity or the loss of substantially all of the biological activity associated with the gene's product. For example, a disrupted msbB gene would be unable to express a MsbB protein having substantial activity. A gene can be disrupted by any one of a number of methods known to the art, for example, by deletion mutagenesis or site-directed mutagenesis.

"Expression" refers to the transcription and translation of an endogenous gene or a transgene in a host cell. For example, in the case of antisense constructs, expression may refer to the transcription of the antisense DNA only. In addition, expression refers to the transcription and stable accumulation of sense (mRNA) or functional RNA. Expression may also refer to the production of protein.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

A "transgene" refers to a gene that has been introduced into the genome by transformation and is stably maintained. Transgenes may include, for example, DNA that is either heterologous or homologous to the DNA of a particular cell to be transformed. Additionally, transgenes may include native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

The invention encompasses isolated or substantially purified nucleic acid compositions. In the context of the present invention, for example, an "isolated" or "purified" DNA molecule is a DNA molecule that exists apart from its native environment and is therefore not a product of nature. An isolated DNA molecule may exist in a purified form or may exist in a non-native environment such as, for example, a transgenic host cell. For example, an "isolated" or "purified" nucleic acid molecule, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences and proteins or partial-length proteins encoded thereby are also encompassed by the present invention. By "fragment" or "portion" is meant a full length, or less than full length, of the nucleotide sequence encoding, or the amino acid sequence of, a polypeptide or protein.

A "mutation" refers to an insertion, deletion or substitution of one or more nucleotide bases of a nucleic acid sequence, so that the nucleic acid sequence differs from the wild-type sequence. For example, a 'point' mutation refers to an alteration in the sequence of a nucleotide at a single base position from the wild type sequence.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991; Ohtsuka et al., 1985; Rossolini et al., 1994). A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence," or "polynucleotide" may also be used interchangeably with gene, cDNA, DNA and RNA encoded by a gene (Batzer et al., 1991; Ohtsuka et al., 1985; Rossolini et al., 1994).

"Operably linked" when used with respect to nucleic acid, means joined as part of the same nucleic acid molecule, suitably positioned and oriented for transcription to be initiated from the promoter. DNA operably linked to a promoter is under transcriptional initiation regulation of the promoter. Coding sequences can be operably-linked to regulatory sequences in sense or antisense orientation.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence including a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even include synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter. An "inducible promoter" is a regulated promoter that can be turned on in a cell by an external stimulus, such as a chemical, light, hormone, stress, or a pathogen.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may include additions or deletions (i.e., gaps) compared to the reference sequence (which does not include additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988); the local homology algorithm of Smith et al. (1981); the homology alignment algorithm of Needleman and Wunsch (1970); the search-for-similarity-method of Pearson and Lipman (1988); the algorithm of Karlin and Altschul (1990), modified as in Karlin and Altschul (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988), Higgins et al. (1989), Corpet et al. (1988), Huang et al. (1992), and Pearson et al. (1994). The ALIGN program is based on the algorithm of Myers and Miller, supra. The BLAST programs of Altschul et al. (1990); (1997), are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide includes a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide includes a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. An extensive guide to the hybridization of nucleic acids is found in Tijssen (1993). Generally, highly stringent hybridization and wash conditions are selected to be about 5EC lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The terms "protein," "peptide" and "polypeptide" are used interchangeably herein.

As used herein, a "transgenic", "transformed", or "recombinant" cell refers to a genetically modified or genetically altered cell, the genome of which includes a recombinant DNA molecule or sequence ("transgene"). For example, a "transgenic cell" can be a cell transformed with a "vector." A "transgenic", "transformed", or "recombinant" cell thus refers to a host cell such as a bacterial or yeast cell into which a heterologous nucleic acid molecule has been introduced. The nucleic acid molecule can be stably integrated into the genome by methods generally known in the art (e.g., disclosed in Sambrook et al., 2001). For example, "transformed," "transformant," and "transgenic" cells have been through the transformation process and contain a foreign or exogenous gene. The term "untransformed" refers to cells that have not been through the transformation process.

The term "transformation" refers to the transfer of a nucleic acid fragment into the genome of a host cell, or the transfer into a host cell of a nucleic acid fragment that is maintained extrachromosomally. A "transgene" refers to a gene that has been introduced into the genome by transformation. Transgenes may include, for example, genes that are heterologous or endogenous to the genes of a particular cell to be transformed. Additionally, transgenes may include native genes inserted into a non-native organism, or chimeric genes. The term "endogenous gene" refers to a native gene in its natural location in the genome of an organism. Such genes can be hyperactivated in some cases by the introduction of an exogenous strong promoter into operable association with the gene of interest. A "foreign" or an "exogenous" gene refers to a gene not normally found in the host cell but that is introduced by gene transfer.

"Vector" is defined to include, inter alia, any plasmid, cosmid, phage or other construct in double or single stranded linear or circular form that may or may not be self transmissible or mobilizable, and that can transform prokaryotic or eukaryotic host either by integration into the cellular genome or exist extrachromosomally, e.g., autonomous replicating plasmid with an origin of replication. A vector can include a construct such as an expression cassette having a DNA sequence capable of directing expression of a particular nucleotide sequence in an appropriate host cell, comprising a promoter operably linked to the nucleotide sequence of interest that also is operably linked to termination signals. An expression cassette also typically includes sequences required for proper translation of the nucleotide sequence. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus.

The term "wild type" refers to an untransformed cell, i.e., one where the genome has not been altered by the presence of the recombinant DNA molecule or sequence or by other means of mutagenesis. A "corresponding" untransformed cell is a typical control cell, i.e., one that has been subjected to transformation conditions, but has not been exposed to exogenous DNA.

A "vaccine" is a compound or composition that will elicit a protective immunological response in an animal to which the vaccine has been administered. An immunological response to a vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest.

As used herein, the term "therapeutic agent" refers to any agent or material that has a beneficial effect on the mammalian recipient. Thus, "therapeutic agent" embraces both therapeutic and prophylactic molecules having nucleic acid or protein components.

II. Virulence Factors of N. meningitidis

One of the major virulence factors of N. meningitidis is the capsular polysaccharide. The capsule aids the bacteria by protecting them from host immune defenses. N. meningitidis serogroups are based on the capsular polysaccharide. Five serogroups, A, B, C, Y, and W-135, are most often associated with invasive meningococcal strains. Polysaccharide vaccines have been developed for serogroups A, C, Y, and W-135. Additionally, recent work on polysaccharide-conjugate vaccines has shown improved efficacy of these vaccines in infants and young adults (Richmond et al., 2001; Zhang et al., 2001). Currently a vaccine for serogroup B is not available.

The capsular polysaccharide for this serogroup is poorly immunogenic due to its similarity to human neural adhesion molecules (West et al., 2001).

An additional virulence factor present in N. meningitidis is lipooligosaccharide (LOS). LOS is the principle glycolipid present in the outer membrane of N. meningitidis, and is composed of the oligosaccharide chain extensions, the core, and the lipid A. The oligosaccharide chain extensions have been shown to play a role in molecular mimicry (Harvey et al., 2001; Preston et al., 1996; Vogel et al., 1999). The lipid A of N. meningitidis is similar in structure to lipid A from other Gram-negative bacteria (Kulshin et al., 1992; Lee et al., 1995; Sunshine et al., 1997), and is known to be responsible for many of the adverse effects seen with Gram-negative bacterial infections (Kulshin et al., 1992; Raetz, 1993). The lipid A, also referred to as endotoxin, over-stimulates the immune system (Raetz et al., 1991), which may lead eventually to shock and death.

III. Lipid A Biosynthesis in N. meningitidis

Steeghs et al. have reported a *N. meningitidis* that is viable in spite of an early block in lipid A biosynthesis (Steeghs et al., 1998). The protein LpxA adds the O-linked 3-OH fatty acid to UDP-N acetylglucosamine, which is the first committed step in the lipid A biosynthesis pathway. Steeghs et al. constructed a hybrid lpxA gene in which the meningococcal N-terminal part was replaced by the corresponding part of *E. coli* lpxA. Steeghs et al. reported that the mutation caused a loss of endotoxin activity. However, the resulting mutant had a reduced growth rate when compared to the corresponding wild-type strain (Steeghs et al., 1998).

HtrB and MsbB are the acyl transferases responsible for the addition of the secondary acyl substitutions onto the lipid A (Brozek and Raetz, 1990; Clementz et al., 1997; Nichols et al., 1997). The secondary acyl substitutions are added to the lipid A after the incorporation of two 2-keto-3-deoxyoctulosonic acid (Kdo) groups. Previous work with htrB and msbB mutants demonstrated that the lipid A portion of their LOS and LPS structures were modified (Lee et al., 1995; Post et al., 2002; Somerville et al., 1996; Sunshine et al., 1997). These modified forms of LOS and LPS were reduced in their toxicity (Jones et al., 1997; Nichols et al., 1997), and in their ability to stimulate cytokine secretion (Harvey et al., (submitted); Somerville et al., 1996). Additionally, the *H. influenzae* and *Salmonella enterica* serovar Typhimurium htrB mutants were also reduced in their virulence (Jones et al., 1997; Nichols et al., 1997).

IV. Vaccine Preparations

The present invention provides a vaccine for use to protect mammals against *N. meningitidis* colonization or infection. For example, the vaccine may contain an immunogenic amount of isolated and purified transgenic *N. meningitidis* cell in combination with a physiologically-acceptable, non-toxic vehicle. The transgenic cell contains a disrupted msbB gene, where the disruption results in altered acyltransferase activity, such that the cell has reduced LOS expression as compared to a corresponding wild-type *N. meningitidis* cell. Vaccines of the present invention can also include effective amounts of immunological adjuvants, known to enhance an immune response. The msbB gene can be disrupted, for example, by insertion, deletion or substitution of nucleotides, or a combination of these techniques, such as both deletion of wild-type nucleotide sequences, and insertion of additional nucleotides.

To immunize a subject, the transgenic *N. meningitidis* cell is administered parenterally, usually by intramuscular or subcutaneous injection in an appropriate vehicle. Other modes of administration, however, are also acceptable. For example, the vaccine may be administered orally, or via a mucosal route, such as a nasal, gastrointestinal or genital site. Vaccine formulations will contain an effective amount of the active ingredient in a vehicle. The effective amount is sufficient to prevent, ameliorate or reduce the incidence of *N. meningitidis* colonization in the target mammal. The effective amount is readily determined by one skilled in the art. The active ingredient may typically range from about 1% to about 95% (w/w) of the composition, or even higher or lower if appropriate. The quantity to be administered depends upon factors such as the age, weight and physical condition of the animal considered for vaccination. The quantity also depends upon the capacity of the animal=s immune system to synthesize antibodies, and the degree of protection desired. Effective dosages can be readily established by one of ordinary skill in the art through routine trials establishing dose response curves. The subject is immunized by administration of the neisserial vaccine in one or more doses. Multiple doses may be administered as is required to maintain a state of immunity to the *neisseria*.

To prepare a vaccine, the purified transgenic *N. meningitidis* cell can be isolated, lyophilized and stabilized. The vaccine may then be adjusted to an appropriate concentration, optionally combined with a suitable vaccine adjuvant, and packaged for use. Suitable adjuvants include but are not limited to surfactants, e.g., hexadecylamine, octadecylamine, lysolecithin, dimethyldioctadecylammonium bromide, N,N-dioctadecyl-N'-N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, MPL, aimethylglycine, tuftsin, oil emulsions, alum, and mixtures thereof. Other potential adjuvants include the B peptide subunits of *E. coli* heat labile toxin or of the cholera toxin. (McGhee et al., (1993). Finally, the immunogenic product may be incorporated into liposomes for use in a vaccine formulation, or may be conjugated to proteins such as keyhole limpet hemocyanin (KLH) or human serum albumin (HSA) or other polymers.

V. Antibodies

The antibodies of the invention are prepared by using standard techniques. To prepare polyclonal antibodies or "antisera," an animal is inoculated with an antigen, i.e., a purified transgenic *N. meningitidis* cell, and immunoglobulins are recovered from a fluid, such as blood serum, that contains the immunoglobulins, after the animal has had an immune response. For inoculation, the antigen is preferably bound to a carrier peptide and emulsified using a biologically suitable emulsifying agent, such as Freund's incomplete adjuvant. A variety of mammalian or avian host organisms may be used to prepare polyclonal antibodies against the transgenic *N. meningitidis*.

Following immunization, immunoglobulin is purified from the immunized bird or mammal, e.g., goat, rabbit, mouse, rat, or donkey and the like. For certain applications, particularly certain pharmaceutical applications, it is preferable to obtain a composition in which the antibodies are essentially free of antibodies that do not react with the immunogen. This composition is composed virtually entirely of the high titer, monospecific, purified polyclonal antibodies to the transgenic *N. meningitides* cells. Antibodies can be purified by affinity chromatography, using purified transgenic *N. meningitides* cells. Purification of antibodies by affinity chromatography is generally known to those skilled in the art (see, for example, U.S. Pat. No. 4,533,630). Briefly, the purified antibody is contacted with the purified CR3, or peptide thereof, bound to a solid support for a sufficient time and under appropriate conditions for the antibody to bind to the polypeptide or peptide. Such time and conditions are readily determinable by those skilled in the art. The unbound, unreacted antibody is then removed, such as by washing. The bound antibody is then recovered from the column by eluting the antibodies, so as to yield purified, monospecific polyclonal antibodies.

Monoclonal antibodies can be also prepared, using known hybridoma cell culture techniques. In general, this method involves preparing an antibody-producing fused cell line, e.g., of primary spleen cells fused with a compatible continuous line of myeloma cells, and growing the fused cells either in mass culture or in an animal species, such as a murine species, from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the F(ab) fragment scFv antibodies, as are partially humanized monoclonal antibodies.

Thus, it will be understood by those skilled in the art that the hybridomas herein referred to may be subject to genetic mutation or other changes while still retaining the ability to produce monoclonal antibody of the same desired specificity. The present invention encompasses mutants, other derivatives and descendants of the hybridomas.

It will be further understood by those skilled in the art that a monoclonal antibody may be subjected to the techniques of recombinant DNA technology to produce other derivative antibodies, humanized or chimeric molecules or antibody fragments that retain the specificity of the original monoclonal antibody. Such techniques may involve combining DNA encoding the immunoglobulin variable region, or the complementarity determining regions (CDRs), of the monoclonal antibody with DNA coding the constant regions, or constant regions plus framework regions, of a different immunoglobulin, for example, to convert a mouse-derived monoclonal antibody into one having largely human immunoglobulin characteristics (see EP 184187A, 2188638A, herein incorporated by reference).

VI. Formulations of Vaccine Compounds and Methods of Administration

The vaccine compounds may be formulated as pharmaceutical compositions and administered to a mammalian host, such as a human patient, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu M$, preferably, about 1 to 50 $\mu M$, most preferably, about 2 to about 30 $\mu M$. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be described by the following non-limiting example.

Example 1

Due to the importance of the lipid A structure in pathogenesis, an msbB homologue in *N. meningitidis* was sought. A gene was identified that showed high similarity to the *Escherichia coli* htrB and msbB genes (see Post et al., 2002 and GenBank Accession Number AF428103). The identified gene was cloned, and deletion/insertion mutants were made in a *N. meningitidis* wild-type encapsulated strain, NMB, and a *N. meningitidis* acapsular mutant strain, NMBcap-. These mutants were subsequently designated NMBA11K3 and NMBA11K3cap-respectively. Purified LOS was not able to be isolated from NMBA11K3. Scanning electron microscopy (SEM) and immunotransmission electron microscopy (TEM) demonstrated that the mAb 6B4, which recognizes the LOS epitope Gal 11-4GlcNAc (Apicella et al., 1990), did not label the surface of the NMBA11K3. However, mAb 6B4 was able to label the surface of NMB, NMBcap-, and NMBA11K3cap-. Additionally, mass spectrometric analysis of outer membrane preparations demonstrated that the lipid A specific C12:0 3-OH lipid was absent from the NMBA11K3 outer membrane sample. Based on these observations, the NMBA11K3 mutant does not express LOS in its outer membrane.

Materials and Methods

Bacterial strains, plasmids, and culture conditions. All bacterial strains and plasmids used in this study are described in Table 1.

TABLE 1

Strains and plasmids used in this study

| Strain or plasmid | Genotype, relevant phenotype, or selection marker | Source or reference |
|---|---|---|
| Strains | | |
| *E. coli* DH5α | $F^-$ ΦD80dlacZΔM15 Δ(lacZYA-argF)U169 deoR recA1 endA1 hsdR17($r_K^-m_K^+$) phoA supE44 $\lambda^-thi^-$ 1 gyrA96 relA1 | Life Technologies |
| *N. meningitidis* NMB | wild-type, serogroup B | Stephens et al., 1998 |
| *N. meningitides* NMBcap- | ΔsiaA-siaD, serogroup B | Wyeth-Lederle |
| *N. meningitidis* NMBA11K3 | Kanamycin resistant, msbB mutant | This study |
| *N. meningitidis* NMBA11K3cap- | Kanamycin resistant, msbB mutant, ΔsiaA-siaD | This study |
| Plasmid | | |
| pUC19 | Ampicillin, cloning vector | New England Biolabs |
| pCR2.1 | Ampicillin, cloning vector | Invitrogen |
| pNMBA11pUS19 | Ampicillin, msbB PCR product in pUC19 vector | Post et al., 2002 |
| pNMBA11K3 | Ampicillin, kanamycin, insertion/deletion msbB mutant in pUC19 | Post et al., 2002 |

*E. coli* was grown in Luria Bertani medium at 37° C. and supplemented with appropriate antibiotics. Encapsulated *N. meningitidis* serogroup B strain NMB, was isolated from the blood stream of a patient with meningococcal sepsis. An acapsular mutant of NMB (PBCC7232-NMB ΔsiaA-D) was a gift from Wyeth-Lederle Vaccines and Pediatrics (West Henrietta, N.Y.). *N. meningitidis* organisms were grown on gonococcal agar (GCA) (Becton Dickinson, Sparks, Md.) supplemented with 1% IsoVitaleX™ or on brain heart infusion (BHI) (Becton Dickinson, Sparks, Md.) agar supplemented with 2.5% heat-inactivated fetal calf serum (FCS) at 37° C. in 5% $CO_2$. Liquid cultures of *N. meningitidis* were grown in BHI broth supplemented with 2.5% FCS or in GC broth supplemented with 1% IsoVitaleX™ at 37° C. Kanamycin resistant *N. meningitidis* were grown on supplemented BHI agar plates or in supplemented BHI broth with 50 μg/ml of kanamycin. *N. meningitidis* organisms grown in the presence of kanamycin were grown without $CO_2$. For growth curve cultures, an overnight bacterial culture was used to inoculate a 3 ml culture to an $OD_{600nm\ of}$ 0.05.

Recombinant DNA and transformation methods. Restriction and modifying enzymes were purchased from New England Biolabs (Beverly, Mass.) and Promega (Madison, Wis.). Standard DNA recombinant protocols were performed as previously described (Sambrook et al., 2001). Transformation of *E. coli* with plasmid DNA was done using the $CaCl_2$ method (Hanahan, 1983). Transformation of *N. meningitidis* was performed as previously described (Stephens et al., 1991).

DNA Isolation. Plasmid DNA was prepared using the QIAprep Spin Miniprep kit or the QIAprep Midiprep kit, according to manufacturer's instructions (Qiagen Inc., Valencia, Calif.). Chromosomal DNA was isolated using the Puregene DNA isolation kit (Gentra Systems, Minneapolis, Minn.).

DNA Sequencing and Analysis. DNA sequencing reactions were performed by using dye terminator cycle sequencing chemistry with AmpliTaq DNA polymerase and FS enzyme (PE Applied Biosystems, Foster City, Calif.). The reactions were run on and analyzed with an Applied Biosystems model 373A stretch fluorescence automated sequencer at the University of Iowa DNA Facility. All primers were either commercially available or were purchased from either Genosys Corporation (Aldrich, Milwaukee, Wis.) or from IDT Technologies (Coralville, Iowa). Sequence analysis was performed using Assembly LIGN, version 1.0 (Oxford Molecular Group Inc., Oxford, United Kingdom), MacVector (Oxford Molecular Group Inc., Oxford, United Kingdom), and Wisconsin Package, version 10.0 (Genetics Computer Group, Madison, Wis.).

Cloning and mutagenesis of the N. meningitidis msbB gene. Cloning and mutagenesis of the msbB gene was performed as previously described (Post et al., 2002). Briefly, the E. coli htrB gene was used to search the Neisseria gonorrhoeae strain FA1090 sequence at the University of Oklahoma website. The sequence that showed highest homology to the E. coli gene was used to design PCR primers. Since the genomes of N. gonorrhoeae and N. meningitidis are highly homologous, primers gchtrB3 5'-CAACAGGCGGCGGTG-GAACAG-3' (SEQ ID NO:1) and gchtrB4 5'-TTCGGCATC-CACTCCCCTTTG-3' (SEQ ID NO:2) were used for amplification of the N. meningitidis strain NMB msbB gene. The N. meningitidis strain NMB msbB gene is represented by SEQ ID NO:3, and the MsbB protein is represented by SEQ ID NO:4. The 1,443-bp PCR product was cloned into the TA cloning vector pCR2.1 (Invitrogen, Carlsbad, Calif.) and was subsequently subcloned into pUC19. This construct was transformed into E. coli DH5 cells (Invitrogen) and was subsequently designated pNMBA11pUC19. Restriction enzymes BclI and BssHII deleted 138 bp from the msbB gene. A kanamycin resistant cassette was inserted into the modified msbB gene, and this construct was designated pNMBA11K3. The proper construct was confirmed using PCR and restriction enzyme digests. Plasmid DNA from pNMBA11K3 was used for the transformation with N. meningitidis strains NMB and NMBcap-. Transformants were selected for on BHI plates containing kanamycin.

Southern blot and PCR analyses. Hybridization experiments were carried out according to manufacturer's protocols. All probes were labeled using either PCR labeling or random labeling with digoxigenin (DIG) labeled dNTP's (Boehringer Mannheim Corp., Indianapolis, Ind.). Primers gchtrB 3 and 4 were used to perform PCR reactions.

SDS-PAGE and Western blot analyses of isolated LOS. LOS was isolated from 6 L of BHI broth supplemented with 2.5% FCS for strains NMB and NMBcap- and 6 L of BHI broth supplemented with 2.5% FCS and 50 µg/ml of kanamycin for strain NMBA11K3cap- by a modified hot-phenol-water preparation (Post et al., 2002). Samples were run on a Tris-Tricine SDS-PAGE as previously described by Lesse et al. (1990). Silver staining was done according to a previously described protocol by Tsai and Frasch (1982). Western blot analysis was performed as previously described by Towbin et al. (1979). MAb 6B4, which recognizes the terminal Galβ1-4GlcNAc moiety of the oligosaccharide chain extension (Apicella et al., 1990), was utilized to detect LOS. The porin antibody 3H1 was a gift from Milan Blake (Baxter Hyland Immuno, Columbia, Md.). The mAb 6B4 was diluted 1:2000 in 1% bovine serum albumin (BSA) in Tris buffered saline with Tween 20™ (TBST), the secondary antibody, goat anti-mouse IgM HRP was diluted 1:20,000 in 1% BSA TBST. The blot was developed using the Super Signal West Pico chemiluminescent substrate according to manufacturer's instructions (Pierce, Rockford, Ill.).

Scanning electron microscopy (SEM) and transmission electron microscopy (TEM) analyses. For microscopy studies, all bacterial strains were grown in BHI broth to an $OD_{600nm}$ of 0.8-1.0. Samples for TEM analysis were placed in an equal volume of 4% paraformaldehyde (final concentration 2%). Samples for SEM analysis were settled onto silicon wafers and fixed in 2% paraformaldehyde. Cells for immuno-TEM were dehydrated using a standard graded ethanol series, followed by embedment in London Resin White (Ted Pella Inc., Redding, Calif.). For resolution of cell membrane morphology by TEM, bacterial cells were treated with osmium according to standard protocols and then dehydrated through graded ethanols and embedded in Epon acrylic resin. These mutations should not have a polar effect on downstream genes. First, a kanamycin cassette, which has previously been shown to produce nonpolar mutations (Menard et al., 1993), was utilized to construct the pNMBA11K3 mutant. Second, the msbB gene is not part of an operon. Over 200 bp of DNA downstream from the msbB gene was sequenced, and no open reading frames were found. In addition, the annotated sequence from N. meningitidis strain MC58 indicates that the closest gene is almost 300 bp downstream from the msbB gene, and it is transcribed in the opposite orientation. Thin sections of embedded cells were mounted on nickel grids. Samples for SEM and TEM were treated with neuraminidase (1 u/ml, Oxford GlycoScience, Novato, Calif.) for 2 h at 37° C. prior to labeling with mAb 6B4, which recognizes the terminal Galβ1-4GlcNAc moiety of the LOS (Apicella et al., 1990). Following overnight incubation with the primary antibody, specimens were incubated with goat-anti-mouse Ig-M conjugated to gold beads. 12 nm gold bead-conjugate (JacksonImmunoResearch, West Grove, Pa.) was used for TEM and 25 nm gold bead-conjugate was used for SEM (EMS, Ft. Washington, Pa.). TEM samples were counter-stained with 5% uranyl-acetate. Samples for SEM were incubated in 2.5% glutaraldehyde to cross-link the antibodies, and then processed using a standard graded ethanol series. These samples were carbon-coated before viewing on a Hitachi S-4000 scanning electron microscope (Hitachi, Mountain View, Calif.). TEM samples were viewed using a Hitachi H-7000 transmission electron microscope. All samples were viewed using microscopes located in the Central Microscopy Research Facility at the University of Iowa.

Isolation of and Western Blot Analyses of Membrane Preparations (MPs). Overnight 10 ml broth cultures were harvested by centrifugation at ~3,800×g for 10 min. The cell pellet was resuspended in OMP buffer (50 mM Tris-HCl, 150 mM NaCl, 10 mM EDTA, pH 7.4) and warmed at 56° C. for 30 min. Then, cultures were cooled to room temperature. Cultures were passed through a syringe, using different gauge needles, to shear the cells. The process was repeated ten times for each gauge needle. This procedure was first performed with a 20-gauge needle, then a 22-gauge needle, and lastly a 25-gauge needle. Sheared cells were centrifuged at 16,000×g for 15 min. The supernatant from this spin was centrifuged at 25,000×g for 20 min. The supernatant from this spin was centrifuged at 30,000×g for 20 min. Finally, the supernatant from the previous spin was centrifuged at 100,000×g for 2 h and 15 min. All spins were performed at 20° C. The pellet that was obtained from this spin was glass-like and was used as the sample for SDS-PAGE. Samples were separated on a 4-20% Tris-Tricine gradient gel (Lesse et. al, 1990). Equal quantities of proteins were loaded onto each gel, as determined by spectrophotometric readings. Coomassie blue staining and silver staining were performed according to previously described protocols (Pederson et al., 1976; Tsai and Frasch, 1982). Western blot analyses were performed as previously described by Towbin et al. (1979). The antibody to porin (3H1) was a gift from Milan Blake (Baxter Hyland Immuno, Columbia, Md.). The mAb 6B4 was used as described above. Blots were developed using the Super Signal West Pico chemiluminescent substrate according to manufacturer's instructions (Pierce, Rockford, Ill.).

GC/MS analysis of membrane fatty acids. The MPs from strains NMB, NMBA11K3, NMBcap-, and NMBA11K3cap- were treated with 0.5 ml of 10% w/w $BF_3$-Methanol (Supelco, Bellefonte, Pa.) and heated at 100° C. for 6 h. Samples were allowed to cool to room temperature and then treated with 0.5 ml of saturated NaCl solution, followed by 0.5 ml of HPLC grade hexanes (Aldrich, St. Louis, Mo.). After vortexing and centrifuging, the organic layers were removed and transferred to clean vessels. The aqueous layers were then extracted a second time with 0.5 ml of hexanes. The combined organic layers were evaporated to dryness under a stream of nitrogen, and later redissolved in hexanes for GC/MS analysis. Samples were analyzed using a Hewlett-Packard 5890 gas chromatograph interfaced with a VG70SE mass spectrometer. The gas chromatograph was equipped with an on-column injector (J & W Scientific, Folsom, Calif.) and samples were separated on a 30 m×0.25 mm BPX70 column with a 0.25 μm film thickness (SGE, Inc., Austin, Tex.). The initial oven temperature was 100° C., and after holding there for 5 min, data acquisition was started and the samples were eluted using a temperature gradient from 100° C. to 220° C. at 4° C./min. The carrier gas was helium at ~6 psi. Relative peak areas were measured from the total ion chromatograms for each run and normalized to the C16:0 component.

Results

Cloning and mutagenesis of the *N. meningitidis* msbB gene. The *N. meningitidis* msbB gene was cloned and designated pNMBA11 (Post et al., 2002). A deletion/insertion mutation in msbB was generated as previously described (Post et al., 2002). Briefly, restriction enzyme BclI and BssHII removed 138 nucleotides from the msbB gene. A kanamycin-resistance gene, aphA-3, was ligated into the site of deletion. This construct was transformed into *E. coli* DH5α cells. Restriction enzyme analysis and PCR were used to confirm that the proper construct had been made. This construct was designated pNMBA11K3.

Transformation of pNMBA11K3 into *N. meningitidis* strains NMB and NMBcap- were performed as previously described (Stephens et al., 1991). Selection for transformants was done on plates containing kanamycin. Southern Blot analyses and PCR demonstrated that the proper mutation had been incorporated into the *N. meningitidis* NMB and NMBcap- genomic DNA. These transformants were subsequently designated NMBA11K3 and NMBA11K3cap-, respectively. Proper capsule expression phenotypes for the four different strains were confirmed using mAb 2-2-B, a serogroup B specific capsular antibody, which was a gift from Dr. Wendell Zollinger, WRAIR, Silver Springs, Md.

Comparison of growth rates for *N. meningitidis* strains NMB, NMBcap-, NMBA11K3, and NMBA11K3cap-. In order to determine whether the mutation in the msbB gene had any effect on the growth rate of the bacteria, growth curves were determined. These growth curves demonstrated that there was no difference in the growth rates of strains NMB, NMBcap-, and NMBA11K3cap- (FIG. 1). However, there was a reduction in the growth rate of strain NMBA11K3 compared with the other strains. In the first eight hours of growth, NMBA11K3 reached 50% of the density of the other strains and after 24 hours growth was reduced by approximately one third. The growth curves were performed three times, and the results of all three experiments were consistent.

Characterization of the LOS by SDS-PAGE and Western blot analysis. Silver staining showed that the NMBA11K3cap- LOS migrated through the gel slightly faster than the NMB and NMBcap- LOS (FIG. 2A). The NMBA11K3cap- LOS stained brown instead of black (FIG. 2A). This staining pattern was consistent with previous reports of LPS and LOS isolated from htrB and msbB mutants (Lee et al., 1995; Schnaitman and Klena, 1993; Post et al., 2002). It has been previously demonstrated that mAb 6B4 binds to LOS through the terminal Galβ1-4GlcNAc (Apicella et al., 1990). Western blot analysis was performed using LOS isolated from NMB, NMBcap-, and NMBA11K3cap-. This blot showed that mAb 6B4 reacted with all of the LOS samples tested (FIG. 2B). These results indicated that the oligosaccharide portion of the NMBA11K3cap- LOS was intact. LOS could not be purified from NMBA11K3 using phenol water, proteinase K extraction, and petroleum ether-phenol extraction methods. Subsequent membrane preparations from NMBA11K3 failed to reveal the presence of LOS bands. Hence, purified NMBA11K3 LOS could not be studied on SDS-PAGE or on the Western blot in these experiments.

TEM analyses of mAb 6B4 immunolabeled NMB, NMBA11K3, NMBcap-, and NMBA11K3cap-. FIG. 3 shows micrographs representative of each of the samples. Immunoelectron micrographs of NMB, NMBcap-, and NMBA11K3cap-(FIG. 3, Panels A, C, and D respectively) show the typical *diplococcus* structure of *N. meningitidis* bacteria. These micrographs also show structurally intact membranes, and an electron dense cytoplasm. The NMBA11K3 sample (FIG. 3, Panel B) shows bacteria that still have the coccoid shape but that are somewhat larger than NMB, NMBcap- and NMBA11K3cap- samples. Additionally, there appear to be patches, instead of an even distribution, of electron-dense material in the cytoplasm. Immunoelectron micrographs of NMB, NMBcap-, and NMBA11K3cap- bacteria (FIG. 3, Panels A, C, and D respectively) show the meningococci labeled circumferentially with 6B4. The immunoelectron micrograph of NMBA11K3 bacteria (FIG. 3, Panel B) shows the meningococci labeled with mAb 6B4 predominately in the cytoplasm of the bacteria, with very little or no mAb 6B4 label present on the surface of these bacteria. Higher-power electron microscopy revealed that both NMB and NMBA11K3 had evidence of bilamellar outer membranes (FIGS. 3E and F, respectively).

SEM analyses of mAb 6B4 immunolabeled NMB, NMBA11K3, NMBcap-, and NMBA11K3cap-. FIG. 4 shows micrographs representative of data collected from each of the samples. All strains showed the typical *diplococcus* shape when viewed using SEM analyses. Strains NMB, NMBcap-, and NMBA11K3cap-(FIG. 4, Panels A, C, and D, respectively) showed surface labeling with mAb 6B4. The mAb 6B4 antibody did not label the surface of NMBA11K3 (FIG. 4, Panel B).

SDS-PAGE and Western blot analyses of MPs from NMB, NMBcap-, NMBA11K3, NMBA11K3cap-. Both silver staining and Coomassie blue staining demonstrated that there were differences in the components of the MP from NMBA11K3 compared with NMB, NMBcap-, and NMBA11K3cap- (FIGS. 5A and 5B). Silver staining analysis showed that there was no detectable LOS present in the NMBA11K3 sample (FIG. 5A). Western blot analysis utilizing the mAb 6B4 confirmed the absence of a full-length LOS structure in the MP from NMBA11K3 (FIG. 6B). Examination of the MP also suggested that there were decreases in the levels of at least two other components of the outer membrane, those with molecular masses of 42 and 35 kDa, in NMBAL 11K3 compared with levels in its parent strain, NMB. Western blot analyses determined that the proteins with altered levels were PorA and PorB (FIG. 6A). FIG. 6A shows the decrease in the amount of PorA and PorB present in the NMBA11K3MP. The expected molecular masses of these proteins are approximately 42 kDa for PorA and 35.7 kDa for PorB.

Figure 7:
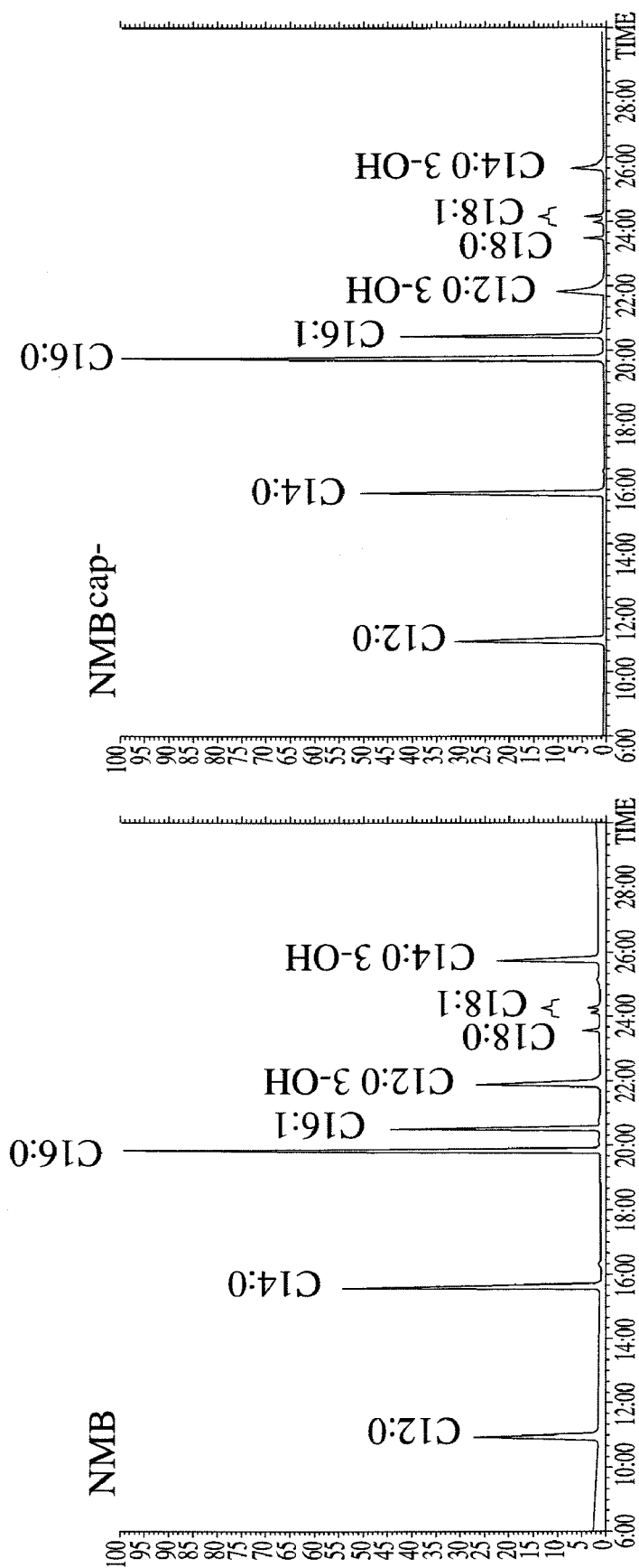
Figure 7:
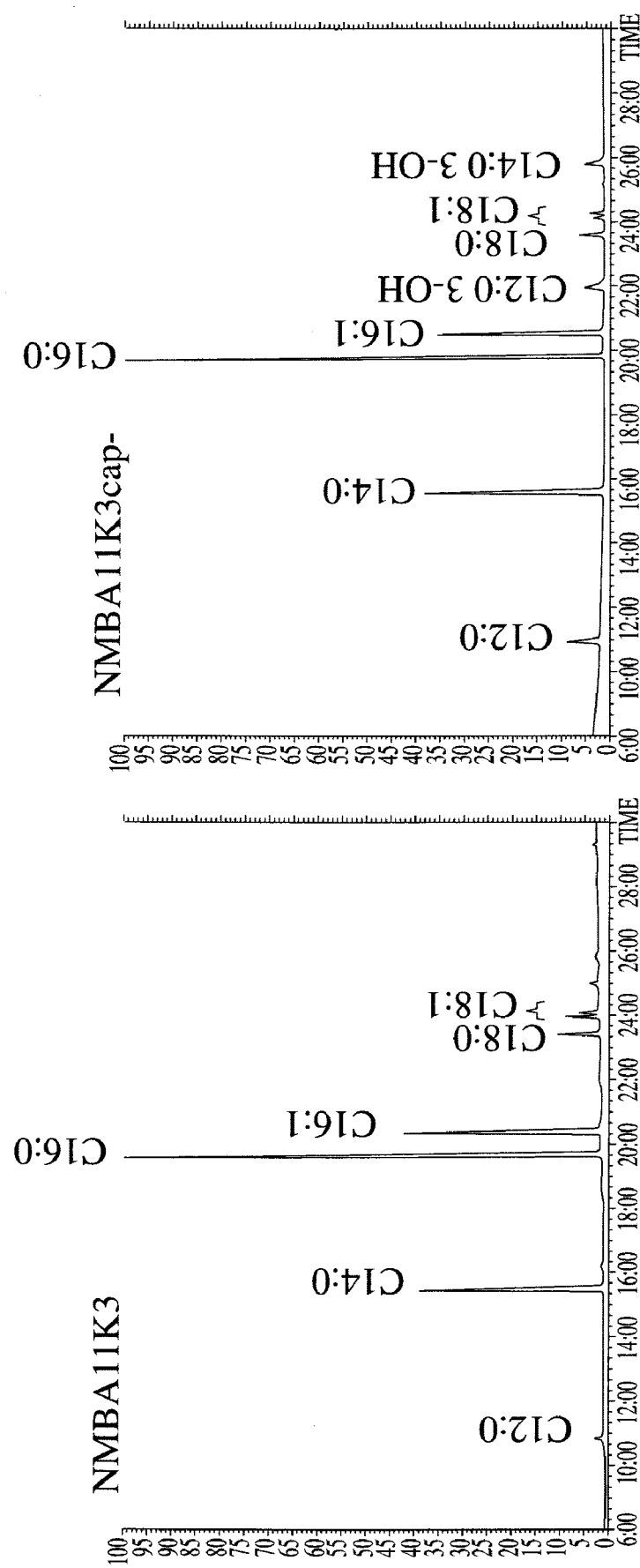

Mass spectrometric analyses of MP Fatty Acids from NMB, NMBcap-, NMBA11K3, and NMBA11K3cap-. Fatty acid methyl esters were prepared from the MPs and were subsequently analyzed by GC/MS (FIG. 7 and Table 2). All of the expected fatty acids were present in each sample; however, the relative abundance of the fatty acids detected from the samples varied. For both the encapsulated and acapsular strains, the hydroxylated fatty acids derived exclusively from lipid A (C12:0 3-OH and C14:0 3-OH) were of lower relative abundance in the msbB mutants than in the parental strains. This phenomenon was most dramatic for the encapsulated strains, where the levels of C12:0 3-OH and C14:0 3-OH were 25-fold and 23-fold higher, respectively, in the NMB sample compared with the NMBA11K3 sample. The NMBcap- sample had C12:0 3-OH and C14:0 3-OH levels that were both approximately 2-fold higher than the NMBA11K3cap- sample. Additionally, the C12:0 fatty acid that is also found in lipid A was recovered in lower relative abundance in the msbB mutants than in their respective parental strains (Table 2). Compared to the lipid A fatty acid ratios in the NMBcap- strain, the relative amounts of C12:0, C12:0 3-OH and C14:0 3-OH detected in the NMBA11K3cap- strain suggest the loss of a single C12:0 fatty acid from the lipid A structure in the msbB mutant. This observation is consistent with molecular weight measurements of the intact lipid As from NMB, NMBcap- and NMBA11K3cap-obtained by matrix-assisted laser desorption ionization-time of flight (MALDI-TOF) mass spectrometry, which showed a shift to lower mass (~182 Da, corresponding to the loss of a lauric acid residue) for the msbB mutant. In the case of the NMBA11K3 mutant, the levels of lipid A fatty acids detected in the OMP were so low that their relative ratios did not give meaningful information about the fatty acid composition of the lipid A. No LOS could be isolated from the NMBA11K3 mutant strain, therefore, MALDI-TOF analysis of the intact lipid A was also not possible. These data demonstrate that the relative abundance of the lipid A fatty acids present in the MPs from the msbB mutants is dramatically reduced compared with their relative abundance in the parental strains. However, this reduction is significantly more pronounced in the encapsulated msbB mutant (NMBA11K3) than in the acapsular msbB mutant (NMBA11K3cap-). These data suggest that the amounts of lipid A, and hence LOS, expressed in the outer membranes of NMBA11K3 and NMBA11K3cap- are significantly reduced compared to their parent strains. Additionally, the relative amounts of C16:0 in the MPs from the msbB mutants were higher than those in the MPs from the wild-type strains. Consistent with these findings, a previous study by Steeghs et al. also found that the relative amounts of short-chain fatty acids increased in a LOS-deficient *N. meningitidis* lpxA mutant (Steeghs et al., 2001).

TABLE 2

| Fatty acid | Relative abundance (%) | | | |
|---|---|---|---|---|
| | NMB | NMBA11K3 | NMBcap- | NMBA11K3cap- |
| C12:0 | 42.1 | 3.2 | 43.2 | 10.0 |
| C14:0 | 63.4 | 42.5 | 51.3 | 40.8 |
| C16:0 | 100.0 | 100.0 | 100.0 | 100.0 |
| C16:1$^9$ | 40.9 | 36.9 | 34.4 | 34.8 |
| C18:0 | 3.1 | 7.5 | 3.1 | 4.6 |
| C18:1$^9$trans | 1.9 | 5.9 | 1.7 | 1.7 |
| C18:1$^9$cis | 2.9 | 3.9 | 3.3 | 2.7 |

TABLE 2-continued

| Fatty acid | Relative abundance (%) | | | |
|---|---|---|---|---|
| | NMB | NMBA11K3 | NMBcap- | NMBA11K3cap- |
| C12:0 3-OH | 37.4 | 1.5 | 18.0 | 8.4 |
| C14:0 3-OH | 30.1 | 1.3 | 10.8 | 6.5 |

Samples were normalized to the C16:0 component.

Discussion

Previous studies involving htrB mutants from *E. coli*, *H. influenzae*, and *S. enterica* typhimurium have demonstrated that they exhibit a number of phenotypes (Karow et al., 1991; Lee et al., 1995; Nichols et al., 1997; Sunshine et al., 1997). *E. coli*, *H. influenzae*, and *S. enterica* serovar typhimurium htrB mutants were all shown to be initially sensitive to temperatures above 32° C. (Karow et al., 1991; Lee et al., 1995; Sunshine et al., 1997). However, work from our laboratory and others have demonstrated that *N. gonorrhoeae* and *E. coli* msbB mutants are not temperature sensitive (Post et al., 2002; Somerville et al., 1996). In agreement with these studies, both NMBA11K3 and NMBA11K3cap- were able to grow on solid medium at 37° C. Growth curves demonstrated that NMBA11K3cap- was able to grow at the same rate as NMB and NMBcap-. However, NMBA11K3 had a slower growth rate, and was unable to reach the same optical density, after 56 hours of growth, as the other three strains. Since the msbB mutants were able to grow at 37° C., and because NMBA11K3cap- was able to grow at the same rate as NMB and NMBcap-, it seems unlikely that the lag in growth of NMBA11K3 is due to temperature sensitivity. A reason for this lag in growth may be found by the examination of the TEM micrographs of NMBA11K3. These micrographs demonstrate that these bacteria appear to have a loosely arranged outer membrane. The TEM studies coupled with the growth curve experiments suggest that the NMBA11K3 have an altered membrane that may make them more susceptible to autolysis.

An additional characteristic of htrB and msbB mutants is modification of the LPS and LOS structures. Studies performed with *S. enterica* serovar typhimurium htrB mutants from *S. typhimurium*, and *H. influenzae* htrB mutants demonstrated that the lipid A structures of both were modified (Sunshine et al., 1997; Lee et al., 1995). The lipid A from the *H. influenzae* htrB mutant was determined to be approximately 90% tetraacyl and 10% pentaacyl instead of the normal hexaacyl structure. Additionally, studies of a *N. gonorrhoeae* msbB mutant demonstrated that the lipid A was pentaacyl instead of hexaacyl (Post et al., 2002). In the studies presented here, we were able to isolate and begin to characterize LOS from NMBA11K3cap-. The increase in migration rate and the change in the staining pattern of the NMBA11K3cap- LOS were consistent with data that has been previously reported for msbB and htrB mutants (Post et al., 2002; Lee et al., 1995; Schnaitman and Klena, 1993). Additionally, the binding of mAb 6B4, which recognizes the terminal two sugars of the oligosaccharide, to NMBA11K3cap- LOS indicates that the oligosaccharide region of the LOS is intact. Similar to findings with the *N. gonorrhoeae* msbB mutant (Post et al., 2002), mass spectrometric analysis of the NMBA11K3cap- lipid A demonstrated that it is missing one lauric acid (C12:0) substitution, and thus may have a pentaacyl rather than hexaacyl structure. These results are consistent with a previous study of an msbB mutant in *N. meningitidis* strain H44/76 msbB mutant (van der Ley et al., 2001).

We were unable to isolate LOS from NMBA11K3 despite using a variety of standard methods. Immuno-SEM using mAb 6B4 demonstrated a lack of surface labeling of NMBA11K3, while NMB, NMBcap-, and NMBA11K3cap-all showed surface binding of the antibody. Immuno-TEM micrographs showed, that unlike what was found for NMB, NMBcap-, and NMBA11K3cap-, there was no mAb 6B4 binding to the outer membrane of NMBA11K3. However, binding of mAb 6B4 was visible in the cytoplasm of NMBA11K3. Since we could not isolate LOS from this mutant, we speculate that this labeling represents the mAb 6B4 binding to the Galβ1-4GlcNAc of the oligosaccharide chain extensions still attached to its carrier, undecaprenol phosphate. The mAb 6B4 has been previously shown to bind to lacto-N-neotetraose-ceramide in human erythrocytes (Mandrell et al., 1988). This study, by Mandrell et al., demonstrated that mAb 6B4 is able to recognize its epitope on a lipid carrier other than lipid A. Recent work in our laboratory with a meningococcal bacA mutant suggests that $N$. $meningitidis$ LOS is assembled in a similar fashion as LPS (D. M. B. Post, A. Zaleski, E. Johansen, B. W. Gibson, and M. A. Apicella, unpublished). Based on these studies, and the current model for LPS assembly (Whitfield, 1995), it appears that the oligosaccharide chain extensions are assembled on the carrier lipid undecaprenol-phosphate. Then, the oligosaccharide chain extensions and the lipid A-core region are transported to the periplasm by separate mechanisms, where they are subsequently ligated and transported to the outer membrane. The failure to isolate the lipid A-core region alone suggests that there is a defect in the assembly of the lipid A-core complex in NMBA11K3. Interestingly, recent findings by Tzeng et al. demonstrated that two $N$. $meningitidis$ strain NMB mutants, defective in Kdo biosynthesis and Kdo transfer to the lipid A, expressed an LOS that consisted only of lipid A (Tzeng et al., 2002(I) and Tzeng et al. 2002(II)). These results demonstrate that the lipid A can be assembled and transported to the bacterial surface in the absence of Kdo.

Mass spectrometric analyses of outer membranes isolated from NMBA11K3 demonstrated that the amounts of the lipid A specific C12:0 3-OH and C14:0 3-OH present in these samples were 25-fold and 23-fold, respectively, less than the amount present in the MP from NMB. These data taken together with the microscopy data suggest that the amount of LOS expressed in the outer membranes of NMBA11K3 is significantly reduced compared to its parent strain. MP from NMBA11K3cap- showed a 2- fold and 1.7-fold decrease in the amount of C12:0 3-OH and C14:0 3-OH, respectively, present in these samples compared to the amount present in MP from NMBcap-. Additionally, the relative amounts of C16:0 in the MPs from the msbB mutants were higher than those in the MPs from their respective wild-type strains. These data suggest that both NMBA11K3 and NMBA11K3cap- are defective in their abilities to assemble their LOS, and that the presence of the capsular polysaccharide makes the defect in LOS assembly and subsequent transport more pronounced. These results suggest that NMBA11K3 may place other lipids, most likely C16:0, the lipid that anchors the capsule to the outer membrane, in their outer membranes to compensate for the loss of the lipid A portion of the LOS. These mutants may preferentially express the lipidated capsule on their surface when the lipid A is altered. However, if the capsule components are absent in the msbB mutant, the meningococcus may be able to incorporate the modified LOS structure into the outer membrane. Interestingly, the LOS deficient $N$. $meningitidis$ lpxA mutant, H44/76(pHBK30), was generated in an encapsulated strain (Steeghs et al., 1998), further suggesting that the C16:0 lipid may have a role in stabilizing the outer membranes of LOS depleted mutants.

Western blot analyses demonstrated that the levels of porin expressed in the outer membrane of NMBA11K3 were also altered. Since porin is known to closely associate with LOS, it was not surprising to see a decrease in the levels of PorA and PorB in the outer membranes. SDS-PAGE analyses of MP from NMBA11K3 demonstrated that a number of other proteins expressed in the outer membrane were present at similar levels to the NMB MP. An explanation for the decrease in the levels of porin and LOS, could be that they are transported to the outer membrane as a complex. The modification in the lipid A structure may have decreased the efficiency of LOS assembly; therefore, the transport and subsequent surface expression of the whole complex is altered.

A decrease in LOS/LPS expression on the bacterial surface has not been previously reported for any htrB or msbB mutant. Previous studies of a $N$. $meningitidis$ msbB mutant by van der Ley et al. did not report any changes in the amount of LOS or porin expressed on the bacterial surface (van der Ley et al., 2001). One explanation for this difference may be the use of different strains of $N$. $meningitidis$ in our studies.

NMBA11K3 will prove to be an important tool for further elucidating the mechanisms of LOS assembly and transport in pathogenic Neisseria. Additionally, since NMBA11K3 is not greatly impaired in its growth rate, and because the surface expression of LOS is reduced, this strain can be used to elicit an immune response against $N$. $meningitidis$.

REFERENCES

Altschul et al., *JMB*, 215, 403 (1990).

Altschul et al., *Nucl. Acids Res.*, 25, 3389 (1997).

Apicella, "*Neisseria meningitidis*", p. 2228-2241, In: Mandell et al., (eds.), *Principles and Practice of Infectious Diseases*, 5th ed, vol. 2. Churchill Livingstone, Philadelphia (2000).

Apicella et al. *J. Infect. Dis.*, 162, 506-512 (1990).

Batzer et al., *Nucl. Acids Res.*, 19, 508 (1991).

Brozek and Raetz, *J. Biol. Chem.* 265, 15410-15417 (1990).

Clementz et al., *J. Biol. Chem.*, 272, 10353-10360 (1997).

Corpet et al., *Nucl. Acids Res.*, 16, 10881 (1988).

Hanahan, *J. Mol. Biol.*, 166, 557-580 (1983).

Harvey et al., *Infect. Immun*., (in press).

Harvey et al., *Mol. Microbiol*, 42, 659-672 (2001).

Higgins et al., *Gene*, 73, 237 (1988).

Higgins et al., *CABIOS*, 5, 151 (1989).

Huang et al., *CABIOS*, 8, 155 (1992).

Jones et al., *Infect. Immun.*, 65, 4778-4783 (1997).

Karlin and Altschul, *Proc. Natl. Acad. Sci. USA*, 87, 2264 (1990).

Karlin and Altschul, *Proc. Natl. Acad. Sci. USA* 90, 5873 (1993).

Karow et al., *J. Bacteriol.*, 173, 741-750 (1991).

Kulshin et al., *J. Bacteriol.*, 174, 1793-1800 (1992).

Lee et. al, *J. Biol. Chem.*, 270, 27151-27159 (1995).

Lesse et. al, *J. Immunol. Methods.*, 126, 109-117 (1990).

Mandrell et al., *J. Exp. Med.*, 168, 107-126 (1988).

McGhee et al. *Sem. Hematol.*, 30, 3-15 (1993).

Meinkoth and Wahl, *Anal. Biochem.*, 138, 267 (1984).

Melaugh et al., *J. Biol. Chem.*, 267, 13434-13439 (1992).

Menard et al., *J. Bacteriol.*, 175, 5899-5906 (1993).

Myers and Miller, *CABIOS*, 4, 11 (1988).

Needleman and Wunsch, *JMB*, 48, 443 (1970).

Nichols et al., *J. Endotoxin Res.*, 4, 163-172 (1997).

Ohtsuka et al., *JBC*, 260, 2605 (1985).

Pearson and Lipman, *Proc. Natl. Acad. Sci. USA*, 85, 2444 (1988).
Pearson et al., *Meth. Mol. Biol.* 24, 307 (1994).
Pederson et al., *Mol. Gen. Genet.*, 144, 339-343 (1976).
Post et al., *Infect. Immun.*, 70, 909-920 (2002).
Preston et al., *Crit. Rev. Microbiol.*, 22, 139-180 (1996).
Raetz et al., *FASEB J.*, 5, 2652-2660 (1991).
Raetz, *J. Bacteriol.*, 175, 5745-5753 (1993).
Richmond et al., *Infect. Immun.*, 69, 2378-2382 (2001).
Rosenqvist et al., *Infect. Immun.*, 67, 1267-76 (1999).
Rossolini et al., *Mol. Cell. Probes*, 8, 91 (1994).
Sambrook et al., *Molecular Cloning: A Laboratory Manual*, 3rd Ed. Cold Spring Harbor Laboratory Press, Cold Spring Harbor, N.Y. (2001).
Schnaitman and Klena, *Microbiol. Rev.*, 57, 655-682 (1993).
Smith et al., *Adv. Appl. Math.*, 2, 482 (1981).
Somerville et al., *J. Clin. Investig.*, 97, 359-365 (1996).
Steeghs et al., *EMBO J.* 20, 6937-6945 (2001).
Steeghs et al., *Nature*, 392, 449-450 (1998).
Stephens et al., *Infect. Immun.*, 62, 2947-2952 (1994).
Stephens et al., *Infect. Immun.*, 59, 4097-4102 (1991).
Sunshine et al., *J. Bacteriol.* 179, 5521-5533 (1997).
Tijssen, *Laboratory Techniques in Biochemistry and Molecular Biology Hybridization with Nucleic Acid Probes*, part I chapter 2 "Overview of principles of hybridization and the strategy of nucleic acid probe assays" Elsevier, N.Y. (1993).
Tzeng et al., *J. Biol. Chem.*, 277, 24103-24113 (2002)(I).
Tzeng et al., *Infect. Immun.*, 184, 2379-2388 (2002)(II).
Towbin et al., *Proc. Natl. Acad. Sci. USA.*, 76, 4350-4354 (1979).
Tsai and Frasch, *Anal. Biochem.*, 119, 115-119 (1982).
van der Ley et al., *Infect. Immun.*, 69, 5981-5990 (2001).
Vogel et al., *Mol. Microbiol.*, 119, 115 (1999).
Vogel and Frosch, *Mol. Microbiol.*, 32, 1133-1139 (1999).
West et al., *Infect. Immun.*, 69, 1561-1567 (2001).
Whitfield et al., *Trends Microbiol.*, 3, 178-185 (1995).
Zhang et al., *Infect. Immun.* 69, 4337-4341 (2001).

All publications, patents and patent applications referred to are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of eliciting an immune response in a subject against *Neisseria meningitidis* comprising administering to the subject a pharmaceutical composition comprising
   (a) a *Neisseria meningitidis* cell comprising a disrupted msbB gene, wherein the cell has a reduced amount of lipooligosaccharide (LOS) present in the cell's outer membrane and/or lipid A components present in the cell's outer membrane as compared to the corresponding wild-type *Neisseria meningitidis* cell, wherein the msbB gene is disrupted by mutagenesis, wherein the cell is *Neisseria meningitidis* NMBA11K3 cell having ATCC designation PTA-7257 or its acapsular mutant NMBA11K3cap-; and
   (b) a pharmaceutically acceptable carrier, wherein the composition is capable of eliciting an immune response against *Neisseria meningitidis*.

2. The method of claim 1, wherein the pharmaceutical composition is administered orally, mucosally or by subcutaneous or intramuscular injection.

3. The method of claim 1, wherein the msbB gene is disrupted by mutagenesis.

4. The method of claim 3, wherein the mutagenesis is a deletion, insertion or substitution mutagenesis, or a combination thereof.

5. The method of claim 1, wherein the cell has a reduced amount of the LOS in its outer membrane as compared to the corresponding wild-type *Neisseria meningitidis* cell.

6. The method of claim 1, wherein the cell has a reduced amount of the lipid A components present in the cell's outer membrane as compared to the corresponding wild-type *Neisseria meningitidis* cell.

7. The method of claim 1, wherein the cell has reduced toxicity as compared to the corresponding wild-type *Neisseria meningitidis* cell.

8. The method of claim 1, wherein the cell is the *Neisseria meningitidis* NMBA11K3 cell having ATCC designation PTA-7257.

* * * * *